(12) United States Patent
Kimmel

(10) Patent No.: US 9,341,464 B2
(45) Date of Patent: May 17, 2016

(54) METHOD AND APPARATUS FOR SIZING AND FITTING AN INDIVIDUAL FOR APPAREL, ACCESSORIES, OR PROSTHETICS

(71) Applicant: Zebadiah M. Kimmel, Cambridge, MA (US)

(72) Inventor: Zebadiah M. Kimmel, Cambridge, MA (US)

(73) Assignee: ATLAS5D, INC., Cambridge, MA (US)

( * ) Notice: Subject to any disclaimer, the term of this patent is extended or adjusted under 35 U.S.C. 154(b) by 28 days.

(21) Appl. No.: 14/352,306

(22) PCT Filed: Oct. 2, 2012

(86) PCT No.: PCT/US2012/058443
§ 371 (c)(1),
(2) Date: Apr. 16, 2014

(87) PCT Pub. No.: WO2013/058978
PCT Pub. Date: Apr. 25, 2013

(65) Prior Publication Data
US 2014/0300907 A1    Oct. 9, 2014

Related U.S. Application Data

(60) Provisional application No. 61/548,079, filed on Oct. 17, 2011, provisional application No. 61/561,627, filed on Nov. 18, 2011.

(51) Int. Cl.
*G01B 11/24* (2006.01)
*G01B 11/00* (2006.01)
(Continued)

(52) U.S. Cl.
CPC *G01B 11/00* (2013.01); *A41H 1/02* (2013.01); *A61B 5/0064* (2013.01);
(Continued)

(58) Field of Classification Search
CPC ......... G06F 3/005; G06F 3/011; G06F 3/017; G06F 3/0488; G06T 2207/30196; G06T 2207/10016; G01B 11/24; G01B 11/005; G01B 11/22
USPC ................. 356/601–623; 382/103, 115, 154; 348/42, 46; 706/12, 48
See application file for complete search history.

(56) References Cited

U.S. PATENT DOCUMENTS 4,406,544 A   9/1983   Takada et al.
4,650,330 A   3/1987   Fujita
(Continued)

FOREIGN PATENT DOCUMENTS

WO   WO01/01354   1/2001

OTHER PUBLICATIONS

International Search Report for PCT/US12/58443 mailed Jan. 10, 2013 (3 pages).
(Continued)

*Primary Examiner* — Hoa Pham
(74) *Attorney, Agent, or Firm* — Choate, Hall & Stewart LLP; William R. Haulbrook

(57) ABSTRACT

A system for sizing and fitting an individual for apparel, accessories, or prosthetics includes at least one energy emitter configured to emit energy onto a field-of-view that contains an individual, and at least one energy sensor configured to capture reflected energy from within the field-of-view. A spatial measurement module calculates spatial measurements of a surface portion of the body of the individual when the individual is either stationary or moving about in real-time, based on data from the energy sensor.

20 Claims, 22 Drawing Sheets

(51) Int. Cl.
*A61F 2/50* (2006.01)
*A61B 5/00* (2006.01)
*G06T 7/60* (2006.01)
*A41H 1/02* (2006.01)
*A61B 5/107* (2006.01)

(52) U.S. Cl.
CPC ............ *A61B 5/1077* (2013.01); *A61B 5/1079* (2013.01); *A61F 2/5046* (2013.01); *G06T 7/602* (2013.01); *A61B 5/1072* (2013.01); *A61F 2002/5001* (2013.01); *A61F 2002/505* (2013.01); *A61F 2002/5049* (2013.01); *G06T 2207/10028* (2013.01); *G06T 2207/30196* (2013.01)

(56) References Cited

U.S. PATENT DOCUMENTS

| | | | |
|---|---|---|---|
| 5,530,652 | A | 6/1996 | Croyle et al. |
| 8,269,834 | B2 | 9/2012 | Albertson et al. |
| 2003/0209893 | A1 | 11/2003 | Breed et al. |
| 2003/0231788 | A1 | 12/2003 | Yukhin et al. |
| 2004/0083142 | A1 | 4/2004 | Kozzinn |
| 2004/0236456 | A1 | 11/2004 | Pieper et al. |
| 2007/0229850 | A1* | 10/2007 | Herber .................. G01B 11/25 356/604 |
| 2007/0252831 | A1 | 11/2007 | Lind et al. |
| 2010/0007717 | A1 | 1/2010 | Spektor et al. |
| 2010/0172567 | A1 | 7/2010 | Prokoski |
| 2010/0191541 | A1 | 7/2010 | Prokoski |
| 2011/0052006 | A1 | 3/2011 | Gurman et al. |
| 2011/0211044 | A1 | 9/2011 | Shpunt et al. |
| 2011/0211754 | A1 | 9/2011 | Litvak et al. |
| 2012/0229634 | A1 | 9/2012 | Laett et al. |
| 2014/0243686 | A1* | 8/2014 | Kimmel ............... A61B 5/1118 600/476 |
| 2014/0279740 | A1 | 9/2014 | Wernevi et al. |
| 2014/0299775 | A1* | 10/2014 | Kimmel ............. G06K 9/00771 250/341.8 |
| 2015/0213702 | A1* | 7/2015 | Kimmel ............... G08B 21/043 382/103 |

OTHER PUBLICATIONS

Loker et al., "Size-specific Analysis of Body Scan Data to Improve Apparel Fit," Journal of Textile and Apparel, Technology and Management, 4(3): 4-6 (2005).

Viktor et al., "Measuring to Fit: Virtual Tailoring through Cluster Analysis and Classification," NRC Publications Archive, entire document (2006).

Written Opinion for PCT/US12/58443 mailed Jan. 10, 2013 (7 pages).

\* cited by examiner

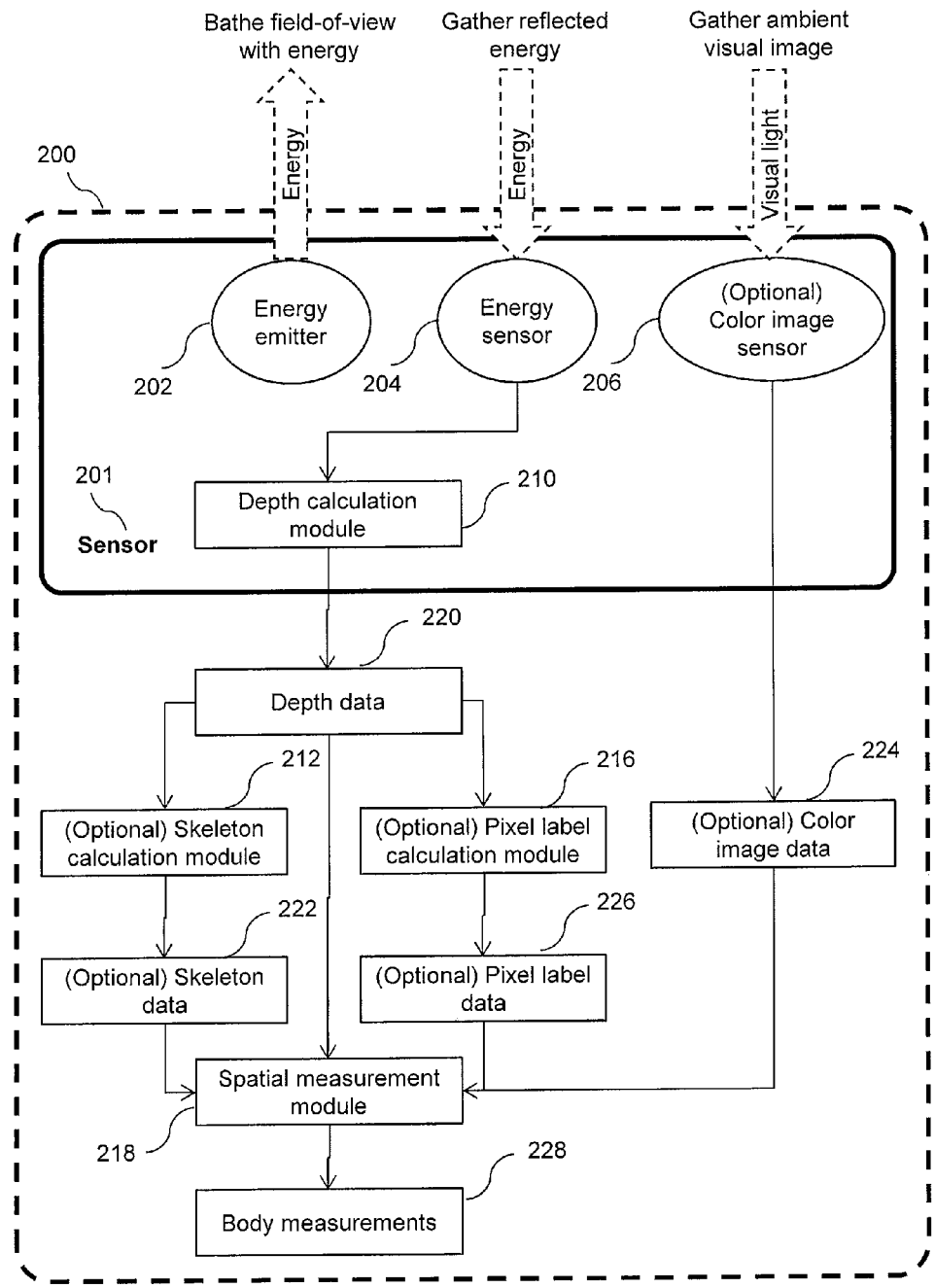

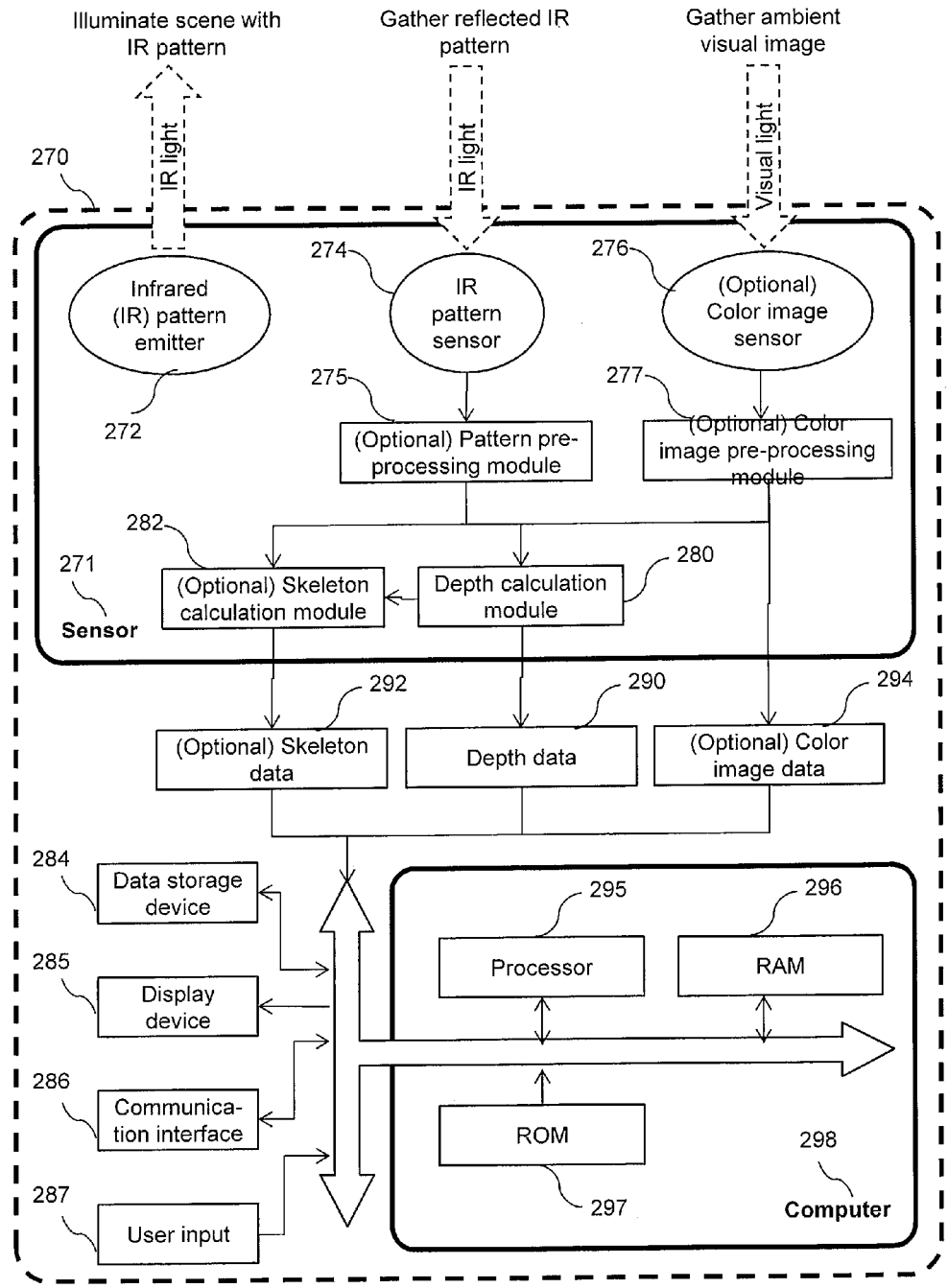

Figure 3
Overhead view
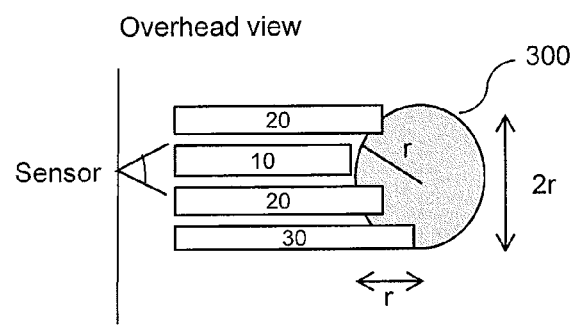
Depth bitmap (view from sensor)
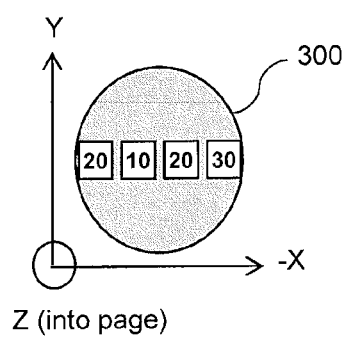

Figure 4

| Measurement | Preferred profile | Alternate profile |
| --- | --- | --- |
| • Upper-arm circumference | • Front | • Side |
| • Shoulder-to-elbow length | • Front | • Side |
| • Shoulder-to-wrist length | • Front | • Side |
| • Shoulder-to-shoulder distance | • Front | • Back |
| • Shoulder slope | • Front | • Back |
| • Neck circumference | • Front | • Side |
| • Head circumference | • Front | • Back |
| • Abdomen volume | • Side | • Front |
| • Abdomen description | • Side | • Front |
| • Torso length | • Front | • Back |
| • Torso width | • Front | • Back |
| • Torso circumference | • Side | • Front |
| • Male chest description | • Front | • Side |
| • Bra cup size | • Side | • Front |
| • Hip-to-knee length | • Side | • Front |
| • Hip-to-heel length | • Side | • Front |
| • Upper-leg circumference | • Front | • Back |
| • Body stance (left- or right-leaning) | • Side | • (None) |
| • Body stance (forward- or backward-leaning) | • Side | • Sole |
| • Foot length | • Front | • Sole |
| • Foot width | • Front | • Palm |
| • Hand length | • Side | • Palm |
| • Hand width | • Side | • Back |
| • Seat volume | • Side | • Back |
| • Seat description | | • (None) |
| • Distance from small-of-back, over crotch, to navel | • Front | • (None) |
| • Eye-to-eye distance | | |

Figure 13
Position user (front view) and calibrator
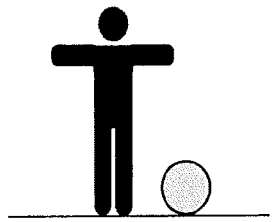
Identify outline of upper arm between elbow and shoulder
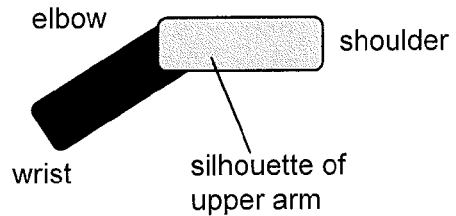
Measure half-circumference of upper arm
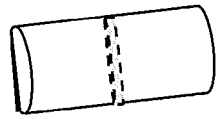
Multiply half-circumference by 2, then scale using calibrator metric to arrive at real-world circumference

METHOD AND APPARATUS FOR SIZING AND FITTING AN INDIVIDUAL FOR APPAREL, ACCESSORIES, OR PROSTHETICS

PRIORITY CLAIM

This application claims the benefit of Provisional Patent Application Ser. No. 61/548,079, filed on Oct. 17, 2011, and Provisional Patent Application Ser. No. 61/561,627, filed on Nov. 18, 2011, both of which are incorporated by reference herein in their entirety.

BACKGROUND OF THE INVENTION

This invention relates to measurements of the surface of a person's body. The term "measurement" as used herein refers to the establishment of a distance, angle, volume, or qualitative description pertaining to one or more portions of an individual's body. Examples of measurements include: the circumference of a person's waist, hip, neck, head, torso, or upper arm; the length of an arm from shoulder to wrist, or of a leg from hip to ankle; the length or width of a foot; an individual's height; the volume and outline of space occupied by an individual's abdomen; or the curve in space that would be described by a ribbon placed starting at the small of the back, then following the surface of the skin across the crotch and up to the navel.

An important use of measurements is to size individuals for apparel, accessories, or prosthetics. The term "apparel" may encompass garments of any kind: shirts, trousers, shoes, hats, etc. The term "accessories" may encompass items that are carried but not generally considered clothing: jewelry, purses, etc. The term "prosthetics" may encompasses devices that replace or augment body parts that are missing or damaged; artificial limbs, orthotic shoes etc.

It is clear that body measurements may be used for many other purposes—such as surgical fitness applications, and biometrics—and although this document will focus on sizing individuals for garments, the scope of the system and method includes all applications that may be realized through measurements of a person's body.

Manual measurement of a person's body has been conducted for thousands of years. Today, the most common way of measuring a person—for example, for sizing a suit—is with a fabric tape measure (often abbreviated to "tape"), optionally accompanied by a set of pins, markers, and pre-sized measurement garments. The tape is used to gauge the length, width, or circumference, of various body portions—for example, the circumference of the neck, or the length of the arm from shoulder to wrist—and the pins, markers, and pre-sized garments are used to mark off the measurements from the fabric tape measure, and to establish the overall shape of volume of the body portion. For example, a pre-sized shirt may be donned by an individual, and then portions of that shirt marked or pinned to confirm to the individual's body shape, in this way creating a physical "shell" or envelope of the person's approximate shape.

Manual measurement suffers from many drawbacks:

It is imprecise. The accuracy of the measurements varies depending on the skill of the measurer the precise location on the body where the measurements are obtained, the stance of the measured individual, and myriad other factors.

It is perishable. The size of au individual changes over time, due to exercise, growth, diet, or even salt intake (affecting tissue volume), so that measurements become stale or obsolete over time.

It is time-consuming. Measurement for a suit, for example, easily encompasses tens of measurements, each of which may take seconds to minutes to accomplish.

It is inconvenient. Because it is infeasible to measure oneself, it is usually necessary for an individual to visit a tailor or garment store to be measured (or at least have a friend do it). The individual typically must travel to the measurement site, wait to be seen, and finally wait to be measured. There is also the inconvenience of potentially being pricked by sharp pins if they are used during the sizing process.

It is resistant to correction. If errors are made during the measurement process, resulting say, an ill-fitting shirt, then the individual must return to the measurer to be re-measured. Furthermore, all the measurements may have to be redone from scratch, because it may not be clear which particular measurement was the cause of the mis-sized garment.

It is not private. It may be embarrassing or uncomfortable for a person to submit to being measured by someone else.

Accordingly, many schemes have been proposed to partially or fully automate the process of body measurement. Some methods of automation in the prior art involve the use of a 3D body scanner. Such a scanner can obtain a complete, essentially "360-degree" 3D scan of a person's body. Common to such methods is emitting electromagnetic or sound energy—such as laser light or sonar—onto a person's body (wherein such energy is transmitted from multiple different directions or angles), and then mathematically reassembling the reflected electromagnetic or sound pattern (as received, again, from multiple directions or angles) to build a complete computer 3D model. Because of the need to transmit and receive the electromagnetic energy from many different directions, 3D scanners must use either many different transmitters and sensors set up simultaneously at different locations around the consumer, or else use an array of transmitters and sensors that rotate, in a tomographic fashion, around the consumer, typically at a fixed rate of angular change.

This burden of transmitters and sensors means that 3D body scanners are necessarily large, complex devices. For example, Unique Solutions manufactures (as of September 2011) the "MyBestFit" "Intellifit Virtual Fitting Room Bodyscanner", which is a human-sized stand-alone box-like device within which an individual stands in order to be scanned by "radio waves". A similar large device is the "NX-16 Whole Body Scanner" manufactured by Shape Analysis Corporation.

3D body scanners suffer from drawbacks. First, their size and complexity prevent them from being used at home; a consumer must travel to a retail store, or tailor, who happens to have installed a 3D body scanner.

Second, it is difficult to use a 3D scanner to generate the types of sizing that are common in the garment industry; even if a mass of, say, 3D mesh data is obtained from the scanner, there remains the need to extract measurements of interest, such as arm circumference or foot length, from that same data; and since the measurements could have as easily been obtained from direct measurements of the person in the scanner, this problem begs the question whether the 3D scanner was even needed in the first place.

Third, because home measurements with a 3D scanner are infeasible, 3D body scanners fail to eliminate the problems of inconvenience and perishable measurements.

Fourth, because of the large amount of data gathered, coupled with the need to rotate sensors around the individual or to perform a raster scan, 3D scanners are typically slow.

Fifth, because 3D scanners cannot be mass-manufactured for use in consumer's homes (for the reasons above), there may be long lines to use the few machines that are assembled, and economies of scale are not available to bring manufacturing costs down.

Sixth, 3D scanners prevent real-time interaction—they do not give real-time feedback, cannot respond in real-time to user commands, and cannot adjust to real-time changes in the user's position. This limits the utility and entertainment value of user interfaces to 3D scanners.

Other methods of automation in the prior art involve the use of special tapes or markers. Common to all such methods is having a person display special markings on their body such its ruled lines, which can then either be manually entered by an operator or automatically measured by a computer program. These methods of automation are necessarily inconvenient (because either the individual to be measured, or another operator, must take the time to learn, assemble, and place the special markers) and prone to error (since the accuracy of measurement depends on the skill with which the special markers are placed). Indeed, these methods of automation do not really automate the measurement of body portions, so much as "parallelize" the manual process of tape measurements.

Other methods of automation in the prior an utilize computerized images of a person, upon which human operators manually superimpose markings which allow relevant garment measurements to be made. Common to all such methods is the requirement for a second person (the operator) to act upon the digitized data, e.g., by using a computer console to manually highlight landmarks on the computerized images. Therefore, these methods do not automate the act of manual measurement, so much as postpone it to a later time or to a different physical location.

Overall, known methods of automated garment sizing suffer from one or more of the following disadvantages:

Known methods may require the use of bulky and/or expensive devices (e.g., 3D body scanners) that are not suited to home but instead require the measured individual to travel to a dedicated location, such as a retail store (meanwhile taking up valuable real estate an that same retail store;

Known methods may generate a complex mass of 3D data which, while comprehensive, nonetheless fails to address the fundamental need to gather a set of specific measurements (e.g., shoulder-to-wrist length) that are the most useful and relevant to garment sizing;

Similarly, known methods may provide an overwhelming amount of detail that is too impractical to act upon for example, high-resolution 3D meshes of the entire body), rather than a well-considered smaller set of specific measurements (for example, shoulder-to-wrist length) that is most practical for manufacturing garments;

Known methods may require an individual to assume odd or uncomfortable positions or poses for extended periods of time;

Known methods may require an individual to keep moving in particular ways, such as rotating continually in circles or adopting a variety of poses, which may distract the individual; prevent the individual from viewing real-time feedback or providing real-time operation of the measurement device; or be difficult for the individual to perform (e.g., if the consumer is physically disabled);

Known methods may be of insufficient precision or resolution to be able to carry out measurements to the desired accuracy;

Known methods may lack the capability to carry the entire range of measurements needed for accurate custom clothing measurements; for example, circumference of a portion of the body;

Known methods may be subject to confounders that limit their accuracy—for example, a purely visual method may be unable to distinguish accurately between an individual's arm and the same individual's section of torso which the arm overlaps Known methods may require substantial manual intervention, by the measured individual and/or a second person, to fill in "missing measurements"; or to confirm the accuracy of automated measurements; or to operate equipment such as a 3D scanner); or to place markers/special clothing on the measured individual's body;

Known methods may be too expensive for individual consumers to purchase.

Known methods require the user to remain still for extended periods of time, typically seconds or even minutes.

Known methods take significant time to produce just a measurement, and if the measurement is erroneous, the measurements MUST be repeated.

Known methods may not allow real-time, interactive user interfaces, or system responses to user movement or commands.

Known methods may obtain limited depth knowledge about a scene, "Depth knowledge" or "depth data", as used herein, refers to gathering information—possibly partial, or incomplete—about the spatial positions of objects in space relative to a known coordinate system, "Image knowledge" or "image data", as used herein, refers to gathering an image of a scene, which may be in visual wavelengths or in other wavelengths of the electromagnetic spectrum. "Color image knowledge" or "color image", as used herein, refers to gathering a visual image of a scene, using color wavelength, similar to the way in which a standard digital camera gathers a visual image. The term "camera", as used herein, refers to any sensor that may gather information about the environment, especially (though not limited to) electromagnetic measurements, such as visible or infrared light. "Camera", as used herein, is thus a general-purpose term, and does not refer specifically to, nor is limited to, visual-light devices.

US patent publication 2011-0211044 (Shpunt) teaches a method of gathering depth knowledge about an object through the use of an illumination module, which projects patterned optical radiation onto a scene, and an image capture module, which captures an image of the reflected pattern.

Image and/or depth data may be combined to identify the spatial location of specific human body portions. US patent publication 2011-0052006 (Gurman) teaches a method of locating portions of a humanoid form using a temporal sequence of depth maps, where each depth map represents a scene as a two-dimensional matrix of pixels indicating topographic information. US patent publication 2011-0211754 (Litvak) teaches a method which processes image and depth data in such a way that specific parts of a body, such as the head, may be identified in the image and depth data. Thus, post-processing of image and/or depth data can generate so-called "skeleton data" or "joint data", describing the approximate locations in space of specific parts of a person's body.

SUMMARY

To substantially overcome the above-described problems, embodiments of the present invention do not rely on 3D body scanners, nor on wearable tapes or markers, to gather information about a scene. Instead, some embodiments of the inventive method and system rely on a minimum number of close-to-instantaneous "data-snapshots" that are each obtained from a single viewpoint, as described below, wherein each data-snapshot contains at least depth data, and preferably a combination of image, depth, skeleton, and or pixel label data. Some other embodiments of the inventive method and system rely on ongoing acquisition of such "data-snapshots," rather than on a minimum number. Body surface measurements, suitable for apparel, accessory, and prosthetic sizing and fitting, are then obtained from one or more such data-snapshots. Embodiments of the present system and method include the following advantages, which are not intended to be an exhaustive list:

- In some embodiments, it may utilize one energy emitter and one camera, in order to obtain depth data;
- In some embodiments, it may utilize one energy emitter, and two cameras of non-overlapping frequencies, in order to obtain at least depth data, and preferably depth data, image data, and skeleton data (which skeleton data may be calculated from the depth and/or image data);
- In some embodiments, it may utilize two cameras that are substantially co-located in space, with similar angles of view onto a scene containing the individual to be measured, such that the overall hardware components easily fit onto a shelf or at the base of a television at home;
- It may conduct each individual measurement using only a single "snapshot" of data in some embodiments; and further, can conduct more than one measurement on the same snapshot; so that the entire measurement process is carried out very rapidly;
- It does not require 3D scanning nor the use of wearable markers; for example, a full 360-degree panoramic view of the individual is not required;
- It is low-cost, compact, portable, and affordable;
- It enables garment-fitting and other applications in an individual's own home;
- It is highly automated and does not require special training or skills to operate;
- It is fast and convenient, allowing an individual to easily take measurements whenever and as often as desired, thus addressing the problem of "perishable" measurements that become inaccurate as time passes;
- It offers privacy, because the individual does not need to travel outside of his/her own home and is able to execute the present system and method alone, and because the present system and method neither collects nor transmits detailed 3D models of the user's body;
- It is able to supply clothing measurements to third-party manufactures for the manufacture and shipping of clothing, accessories, or prosthetics, to the user's home—so that the user may be sized for and purchase such items from home, without the need to visit a retail store or measurement kiosk.
- It is flexible, allowing the user to see "previews" of sized and fitted items at home before making any purchase, and also allowing the user to select his/her preferences or choose different options for personalization.
- It permits the user to move about while body measurements are being acquired, without having to pose, in contrast to a 3D scanner, where the user must remain perfectly still while being scanned.
- It permits multiple measurements to be acquired very rapidly, such that obviously erroneous or outlier measurements may be discarded in real-time, and good-quality measurements may be kept or combined; in contrast to a 3D scanner, where each lengthy scan produces only a single measurement, which if erroneous, requires the entire process to be repeated.
- It enables real-time interactivity with the user, for example, it may adjust or respond in real-time to the user's movements, or communicate useful information (such as "virtual measuring tapes" displayed on a screen) to the user in real-time.

There are many useful applications of this low-cost, convenient, and private system and method of sizing virtually any desired surface portion of a person's body. The following recitation of useful applications is not intended to be an exhaustive list, but merely points out the wide and divergent fields in which embodiments of the present system and method find application.

The present-day difficulty of sizing clothing is easily apprehended. The sizes of clothing items are not consistent across manufactures or countries, and desired sizes are often out-of-stock at retail stores, or simply non-existent. Consumers must typically travel from store to store seeking clothing that fits "well enough". Embodiments of the present system and method prepare standardized types of measurements that are applicable to all types of clothing and that may be translated across all brands.

Although, as noted above, kiosks utilizing 3D scanners are becoming available in the retail setting, they still impose wait times on the consumer, who must go to the location of the scanner; may impose wait times on the consumer, who might have to stand in line behind others to use the 3D scanner; and require the consumer to return to the store if any measurements were missed or have to be repeated. Embodiments of the present system and method are designed to be used at home, as much and as often as the user wishes.

In-store measurements also raise privacy concerns. 3D scanners are necessarily operated by third parties, and the detailed body-shape data that they generate—which may be used to reconstruct nude images—are also stored by third parties, out of the control of the consumer. The system described herein is designed to allow clothing consumers to measure themselves, and then purchase, custom-fit clothing privately and in the comfort and convenience of their own home. The system does not require, use, obtain, nor store full-body 3D scans.

The desire for privacy may assume particular prominence in some special circumstances, such as illness or injury. For example, breast cancer victims who have undergone mastectomies may wish to carry out private measurements to aid in the purchase of specially-shaped bras.

Some embodiments of the system are able to carry out measurements using electromagnetic waves that are only in the visual or near-visual spectrum (e.g., infrared). Such waves are ubiquitous in nature and harmless to humans. The system does not require the use of potentially harmful electromagnetic waves or radiation, e.g., lasers, which pose potential eye hazards, or x-rays.

Similar to the sizing situation for clothing, it is challenging to size accessories, such as necklaces, watches, sunglasses, or hats. For example, it is not unusual for a consumer to be gifted a necklace which doesn't fit correctly, requiring the consumer to take the necklace back to the source store for resizing of the necklace chain. The advantages of the present system and method for clothing apply in equal measure to accessories.

For individuals suffering from medical conditions that require special devices attached to the body, such as orthotic shoes or prosthetic legs, sizing is often an even more arduous process. For example, such individuals may have difficulty traveling to a practitioner who can correctly size them for the device question; and if devices of different sizes need to be purchased over time (for example, a prosthetic leg for a young amputee), the inconvenience and expense are magnified. Embodiments of the present system and method allow individuals who require medical devices or specialty clothing to easily and affordably measure and order the relevant body parts from home, without the need to travel or to incur the expense of seeing a practitioner.

Embodiments of the present system and method can be used to track parameters of the person's body itself (as opposed to items that are worn). This can be useful in the setting of health and fitness, home care, weight loss, diabetes, or other situations where an individual wishes to track their size and shape over time.

Embodiments of the present system and method can be used to generate custom-fit devices for a wide variety of purposes, ranging from consumer to industrial to military—for example, EEG sleep monitors to be worn for sleep studies; body-hugging swimwear; or body armor.

Embodiments of the present system and method are not limited to humans. They may be applied to animals, such as cats, dogs, or horses: for example, if custom clothing, harnesses, or saddles are desired.

It is also possible to continuously execute embodiments of the present system and method over time, thereby creating "movies" of changing measurements—for example, to examine the motion of a muscle, or the change in a person's gait. Time-motion studies of this nature offer potential applications in, for example, medical rehabilitation, surgical recovery, and fall prevention.

The above examples show that embodiments of the present system and method are useful in many applications, ranging from apparel to medicine to animal husbandry to home care:

Specifically, one embodiment of the present method includes:
 a) Identifying a collection of body or worn-garment measurements
 b) (Optionally) Positioning a calibrator device in the field-of-view
 c) Determining the minimum set of user profiles, where each profile corresponds to a different pose of the user in the field-of-view
 d) Selecting an unused profile from the set of profiles in step c)
 e) Positioning the user in the field-of-view in accordance with the profile of step d)
 f) Acquiring a data-snapshot
 g) Collecting a set of measurements from the snapshot
 h) Checking whether all measurements from Step a) have been obtained to a desired level of accuracy or threshold Another embodiment of the present method includes:
 a) Identifying a collection or body or worn-garment measurements
 b) (Optionally) Positioning a calibrator device in the field-of-view
 c) Identifying the user's current profile in the field-of-view
 d) Acquiring a data-snapshot
 e) Collecting a set of measurements from the snapshot
 f) (Optionally) Adjusting or updating the measurements of step e), for example, by averaging over time
 g) (Optionally) Storing the measurements or steps e) and/or f) for use in future iterations of step f)
 h) Checking whether all measurements from step a) have been obtained to a desired level of accuracy or threshold In another embodiment, a method of sizing and fitting an individual for apparel, accessories, or prosthetics includes capturing data corresponding to the individual moving within a field-of-view or remaining stationary for a predetermined amount of time within the field-of view, of at least one pattern emitter and one image capture device; calculating depth data for the field-of-view based on the emitted pattern and received image; and calculating one or more spatial measurements of a portion of a body surface of the individual based on the depth data for the field-of-view.

BRIEF DESCRIPTION OF THE DRAWINGS

FIGS. 2A-2F show block diagrams according to specific embodiments of the present system and method.
FIG. 3 demonstrates the use of a calibrator device.
FIG. 4 shows a lookup table that matches measurements with their preferred and alternate profiles.
FIG. 13 shows an example of obtaining a circumference of a user's upper arm.

DETAILED DESCRIPTION

Figure 1A:
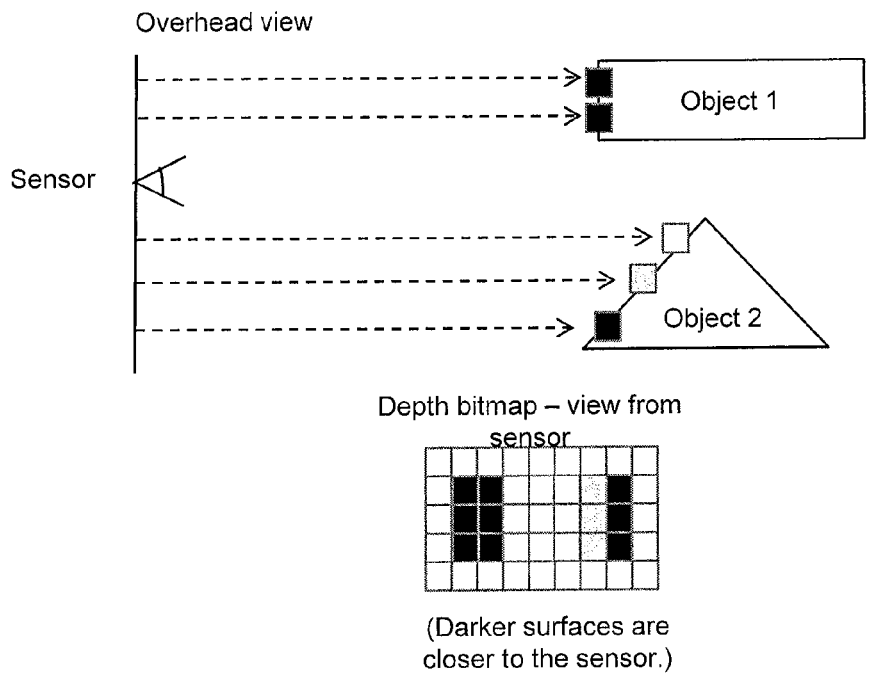
FIGS. 1A and 1B show representations of depth data.

Embodiments the present invention are designed to automate taking physical measurements of portions of a user's body in ways that are compact, portable, private, affordable, repeatable, rapid, and convenient. The system may utilize a single energy sensor to obtain, at a minimum, depth data; or two energy sensors of non-overlapping frequencies to obtain a combination of depth data and spectral data (for example, color image data). Skeleton data (which consists of the approximate locations in space of joints, or of other ambiguous and/or diffuse anatomic structures) may in turn be calculated from the acquired depth and/or spectral data. Pixel label data (which consists of labeling pixels in acquired depth maps or color image maps, such that the labeled pixels correspond to the body surfaces of humans in the field-of-view) may also be calculated from the acquired depth and/or spectral data.

Any collection of distance measurements to (or between) objects in a field-of-view is referred to herein as "depth data". There are many ways to acquire, calculate or otherwise generate depth data for a field-of-view.

For example, depth data may be calculated based on a "time-of-flight" method. In this method, light with known physical characteristics (such as wavelength) is emitted into a field-of-view. An energy sensor, such as a camera, receives the light that is reflected from the field-of-view. Changes in the physical characteristics of the light between its being emitted and its being received—for example, the round-trip transit time of a light raise, or the phase shift of an emitted waveform—allow calculation of the distance to various objects (that reflect the light) in the field-of-view. If light pulses are utilized (for example, to measure round-trip transit time), the emitter can be, for example, a pulsed LED. If continuous light is utilized (for example, to measure phase shift), the emitter can be, for example, a laser. Time-of-flight cameras are a subset of LIDAR (Light Detection and Ranging) technologies, in which emitted-and-reflected light is used to remotely gauge the distance or other properties of a target. LIDAR cameras are similar to radar devices; the main difference is that radar bounces radio waves off target objects, but LIDAR uses ultraviolet, visible, or near-infrared light, Mesa Imaging AG, of Zurich, Switzerland, is an example of a company that manufactures devices to acquire depth data through time-of-flight: for example, its SR4000 time-of-flight camera.

Besides LIDAR, a different method of calculating depth data is through the use of "pattern deformation methods," also sometimes called "light coding". In pattern deformation methods, a light pattern with known physical characteristics (such as pattern shape and spacing) is emitted into a field-of-view. An energy sensor, such as a camera, receives the light pattern that is reflected from the field-of-view. Changes in the pattern between its being emitted and its being received—for example, gridlines moving closer further apart, or average distances between speckled dots growing or shrinking—allow calculation of the distance to various objects (that reflect the light) in the field-of-view.

In contrast to time-of-flight or LIDAR, the specific wavelengths or transit of the emitted light are not crucial; what matters in pattern-deformation methods are the emitted pattern in which the light is placed, and how that emitted pattern is subsequently reflected and deformed by objects in the field-of-view. Because the specific wavelength is less important in pattern-deformation methods, a common choice of wavelength in such methods is infrared, which light cannot be seen by the human eye, and can be superimposed on a scene without disturbing people. If the light pattern is relatively fixed and constant, it is called "structured light"—often, structured-light patterns are grids of regular lines.

If the light pattern exhibits random or pseudorandom variation, it is called "coded fight"—often, coded-light patterns are lattices of dots. (The reason why random or pseudorandom variations may be used light patterns is so that small areas of the pattern will "took slightly different" compared to each other, enabling easier lining-up and registration of the emitted and reflected patterns.) PrimeSense Limited, of Tel Aviv, Israel, is an example of a company that manufactures sensors to acquire depth data through pattern deformation: its sensors are embedded in, for example, the Microsoft Kinect device (Microsoft Corp., Seattle, USA) and the Asus Xtion device (Asustek Computer Inc., Taipei, Taiwan).

Besides time-of-flight, LIDAR, and pattern deformation, a different method of acquiring depth data is through the use of emitted energy that is not light. For example, sound (rather than light) may be emitted and bounced off objects; the reflected physical characteristics of the sound, such as round-trip transit time, or frequency or phase shift, may be used to calculate depth or other characteristics of the objects in the field-of-view. Sommer Mess-Systemtechnik, of Koblach, Austria is an example of a company that manufactures devices to acquire depth data through ultrasonic impulse: for example, its USH-8 sensor, which uses ultrasonic impulses to measure snow depth.

Embodiments of the present invention may use any type of entitled and received energy, including but not limited to visible light, ultraviolet light, infrared light, radio waves, audible sound waves, ultrasonic frequencies, and pressure vibrations, in order to acquire depth data. Embodiments of the present invention are agnostic as to the source of depth data. As used herein, "depth data" refers to measurements of the distances to objects (or portions of objects) in a field-of-view.

Note that the term "camera" is used herein for convenience only, and any energy sensor, or image capture device, or energy capture device, or data capture device using various ranges of electromagnetic radiation or other types of energy may be used and substituted therefore. The terms "energy sensor", "camera," "image capture device." "energy capture device," and "data capture device" are used interchangeably herein. Some such devices need not emit electromagnetic radiation, because they capture energy based on reflected radiation already present in the environment. Other such devices may emit electromagnetic radiation and capture reflected radiation, such as ultrasonic transducers, and the like, where such emitted electromagnetic or other energy radiation is not present in the environment to a sufficient degree or sufficiently present in known directions relative to a target.

Additionally, the number of energy sensors are not limited to one or two such devices: one energy sensor, two energy sensors, or more than two energy sensors may be used (for example, to generate additional stereoscopic data, or to cover a larger region of space), as well as a single energy sensor.

"Image data" or "image" as used herein may refer to data or image captured by any of the above-mentioned devices or sensors, such as an energy sensor, a camera, an image capture device, an energy capture device, and/or a data capture device, and need not necessarily refer to the optical range, in one embodiment, image data may refer to the same visual-spectrum data that would be generated by a standard digital camera, consisting of a 2D photographic pixel map, where each pixel represents a visible color. Note that in general, "color" as used herein may refer to all the colors et the visual spectrum or a grayscale spectrum, or any other palette of visual colors that are perceptible by the human eye. As used herein, "color image data" refers to visual (visible to the human eye) image data, similar to that captured by a standard consumer digital camera.

Figure 1B:
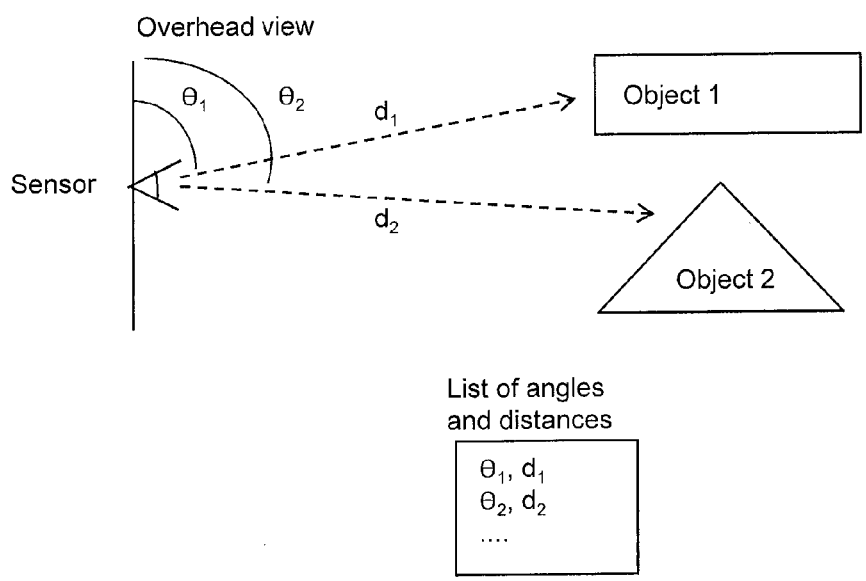

"Depth data" is less intuitive than color image data. Depth data represents the distance from a sensor to a nearest object in space. FIGS. 1A and 1B show two representations of depth data. The preferred representation of depth data, shown in FIG. 1A, is a 2D bitmap, also sometimes referred to as a depth map. However, alternate representations are also possible. The value of each (x, y) pixel in the 2D bitmap shown in FIG. 1A represents the distance from a common reference plane—typically a vertical plane established by the sensor itself, with the x-axis running horizontally, and the y-axis running vertically—to the closest physical object, along a normal ray projected outward from the common reference plane at that (x, y) coordinate. (In such a coordinate system, since the y-axis extends floor-to-ceiling, and the x-axis extends to left-and-right, of the sensor, it follows that the z-axis extends straight out from the sensor into the field-of-view.)

A 2D depth data bitmap therefore corresponds to a quantized contour, or topographic, map of the sensor's field-of-view. Equivalently, a pixel value z at position (x, y) in the data bitmap indicates that the surface (or edge) of a real-world object exists at coordinate position (x, y, z) in physical space.

A depth bitmap can represent, depth data only for aspects of an object that are visible to the sensor: any aspects of an object that are out-of-view of the viewpoint are "invisible" and not represented in the depth bitmap.

For example, if we were to obtain a depth data bitmap of the Moon as taken from standing on the Earth, we would find that a collection of pixels in the middle of the bitmap formed the shape of a circle. The pixels in the center would have, the lowest distance values (they would correspond to the central part of the Moon which is closest to the Earth), and the pixels at the edge of the circle would have the highest distance values (they would correspond to the edge of the visible face of the Moon). Pixels outside the circle, of the Moon, representing the void of space, would have maximum distance values (essentially equivalent to infinity). The "dark side of the Moon", invisible to us, would not be represented in the bitmap at all.

FIG. 1B shows an alternate representation of depth data, in which the positions of objects in the field-of-view are described using a list of angles and distances. Such a representation is not as advantageous as the bitmap approach, due to the complexity of "working backwards" to identify which objects are placed where in space.

FIG. 2A shows a block diagram of an embodiment of the present method and system. A system for sizing and fitting an individual for apparel, accessories, or prosthetics (the system) is shown generally as 200, which may be used to carry out the method disclosed described in this document. As set forth above, any form of active energy capture (emission of energy and capture of the reflected energy) or passive energy capture (capture of reflected energy based on ambient energy sources) may be used.

As shown in FIG. 2A, energy emitter 202 bathes the field-of-view with energy. As described previously, the energy emitted may comprise visible light or non-visible light, or sound, or any other type of energy. The energy emitted may bathe the entire field-of-view all at once, or may bathe different parts of the field-in-view in turn. Energy sensor 204 gathers the energy that is reflected or received from objects in the field-of-view. Depth calculation module 210 calculates the distances to objects in the field-of-view using the information acquired by energy sensor 204. As described previously, such depth calculation may performed using time-of-flight, or LIDAR, or pattern deformation, or any other method suitable for calculating depth measurements. Depth calculation module supplies depth data 220, where, for example, depth data 220 may be structured in a form similar to that shown in FIG. 1A.

In FIG. 2A, depth calculation module 210 uses the captured energy data from energy sensor 204 to calculate depth data 220 corresponding to the objects in the field-of-view. Such calculation may also rely on knowledge of the characteristics of the most recent energy characteristics or energy patterns emitted by energy emitter 202, and/or on past energy characteristics or energy patterns emitted by energy emitter 202, or captured by energy sensor 204, or on any other information required to carry out depth calculations.

Sensor portion 201 encapsulates a minimal set of components required by some embodiment of the present inventive method, viz., an energy emitter, an energy sensor, and a depth calculation module. Because of the similarity to energy sensor 204, optional color image sensor 206 is included for convenience within sensor portion 201. It is important to note that sensor portion 201 is a label of convenience, roughly corresponding to the typical hardware components required for some real-world embodiments of the present inventive method, and so any components of the present inventive method, including all of those, for example, shown in FIG. 2A, may be brought in or out sensor portion 201. For example, optional skeleton calculation module 212 could appear inside sensor portion 201 in some embodiments of the present inventive method.

The depth data 220 may be used by optional skeleton calculation module 212 in order to construct optional skeleton data 222, consisting of a set of approximate spatial locations of anatomic joints (e.g., the [x, y, z] locations of shoulder, hip, and ankle). The data from depth calculation module 220 may also be used by optional pixel label calculation module 216 in order construct optional so-called "pixel label" data 226, consisting of labeling individual pixels in a depth map (such as the depth map shown in FIG. 1A) that correspond to a human being in the field-of-view. A wide variety of machine learning methods are known in the art that may be utilized by optional skeleton calculation module 212 and optional pixel label calculation module 216, and are not discussed further here.

Spatial measurement module 218 uses depth data 220 to calculate measurements in space, as described further below. Spatial measurement module 218 supplies body measurements 228. For example, a body measurement 228 might be the distance between the most-lateral point of an elbow, and the ulnar bone of an arm.

It is possible to calculate body measurements using only depth data 220; however, the accuracy of the depth pattern, or of body measurement calculations derived from depth data alone, may insufficient, and it may also be difficult to clearly delineate separate objects using depth data alone. Therefore, in some applications it may be preferable to also include a standard color image sensor 206, which gathers visual data in the same way as a standard digital camera. Optional color image sensor 206 supplies optional color image data 224.

For example, if two objects in the field-of-view are close together, such that the energy received by energy sensor 204 does not lead to clearly distinguishable depth data 220, their different visual colors received by the color image sensor 206 may be used to help distinguish the objects front each other. However, for many applications of system 200, the color image sensor 206 and the color image data 224 are optional.

As noted above, it is possible to calculate body measurements using only depth data 220. However the speed of body measurement calculation may be improved by drawing upon additional calculations performed on depth data 220. For example, optional skeleton data 222 may be calculated from depth data 220, and used to improve the speed of calculating body measurements 228. For example, optional label data 226 may be calculated from depth data 220, and used to improve the speed of calculating body measurements 228. As described previously, optional skeleton data 222 describes the approximate spatial locations of anatomic joints (for example, the three-dimensional [x, y, z] locations of shoulder, hip, and ankle). As described previously, optional pixel label data 226 distinguishes which pixels in a depth map (if any) correspond to a human being, and which do not.

In FIG. 2A, the depth data 220 consists of a set of calculated depth data, where such data may conform, for example, to the representation shown in FIG. 1A. The optional color image data 224 consists of a set of image data; such data may, for example, be represented in the way as images that are acquired by a typical everyday consumer digital camera, such as by using a pixel array or raster. The optional skeleton data 222 consists of a set of calculated spatial measurements of the approximate locations of portions of a user's body, for example, shoulders and knees; such data may, for example, be represented by a set of (x,y,z) coordinates. The optional pixel label data 226 consists of a set of pixel labels delineating which pixels correspond to a human being in the field-of-view; such data may, for example, be represented by a pixel array or raster.

Embodiments of the system 200 preferably utilize a combination of depth data 220, optional color image data 224, optional skeleton data 222, and optional pixel label data 226, to conduct measurements of an individual's body surface. The system 200 can utilize depth data 220 alone, at the potential cost of decreased accuracy and/or speed.

The sensor portion 201 of FIG. 2A may alternately utilize more than two image sensors. For example, the sensor portion 201 of FIG. 2A may be augmented with a third image sensor (not shown), which may overlap in energy type or frequency with either the energy sensor 204 or the optional color image sensor 206, in order to provide an additional nearby stereoscopic vantage point by which to increase accuracy of depth calculations. Or, multiple sensor portions 201 may be combined for example, by placing a different sensor portion 201 in several fitting rooms of a store, then combining together their collective data to cover a larger area than a single sensor portion 201 is capable of covering.

Figure 2B:
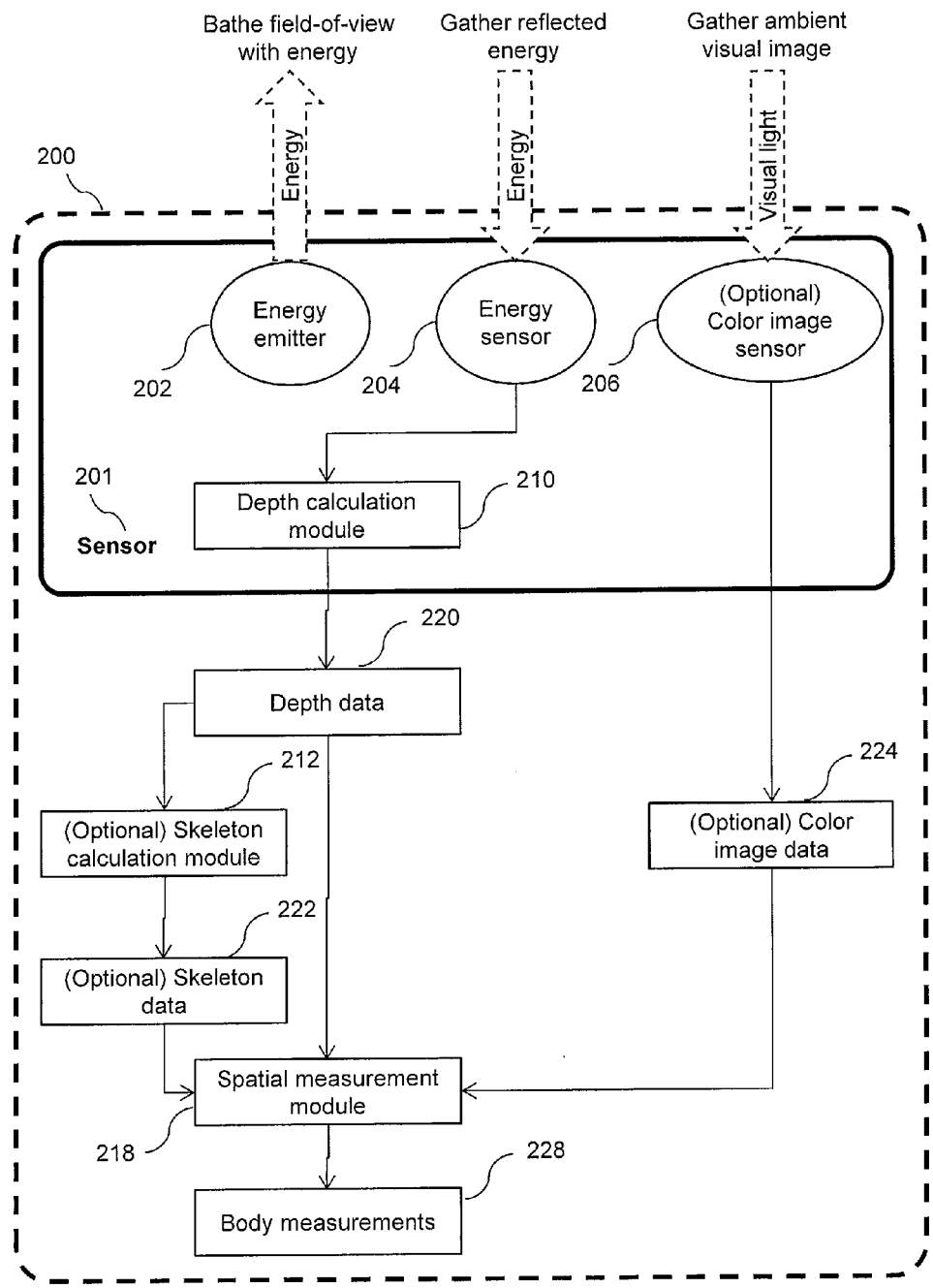

FIG. 2B shows another embodiment of the present inventive method. FIG. 2B is similar to FIG. 2A, except that optional pixel label calculation module 216 and optional pixel label data 226 of FIG. 2A are omitted, to emphasize that they are not required for some embodiments. All items in FIG. 2B correspond to their like-numbered items in FIG. 2A.

Figure 2C:
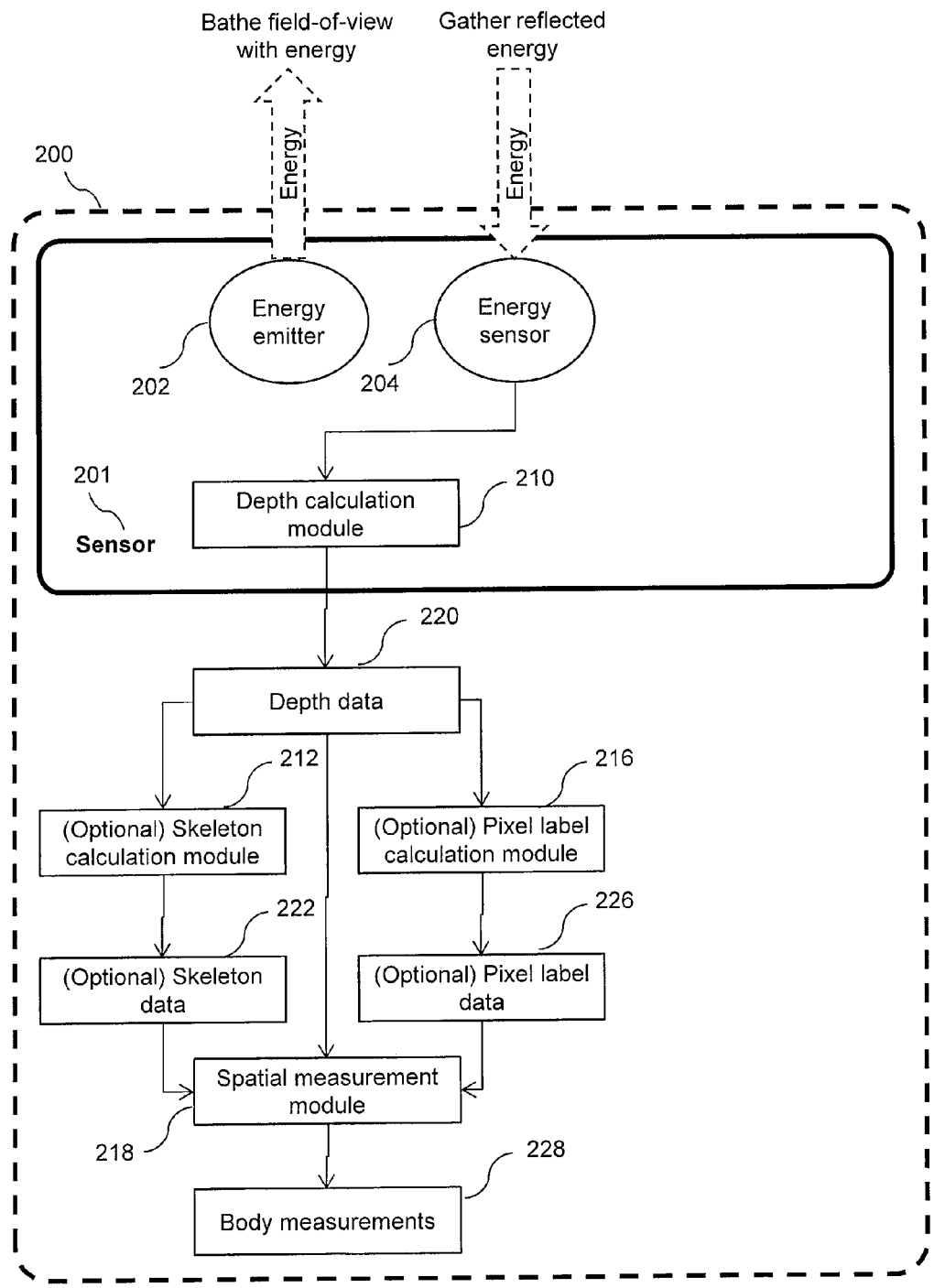

FIG. 2C shows another embodiment of the present inventive method. FIG. 2C is similar to FIG. 2A, except that optional color image sensor 206 and optional color image, data 224 of FIG. 2A are omitted, to emphasize that they are not required for some embodiments of the present inventive method. All items in FIG. 2C correspond to their like-numbered items in FIG. 2A.

Figure 2D:
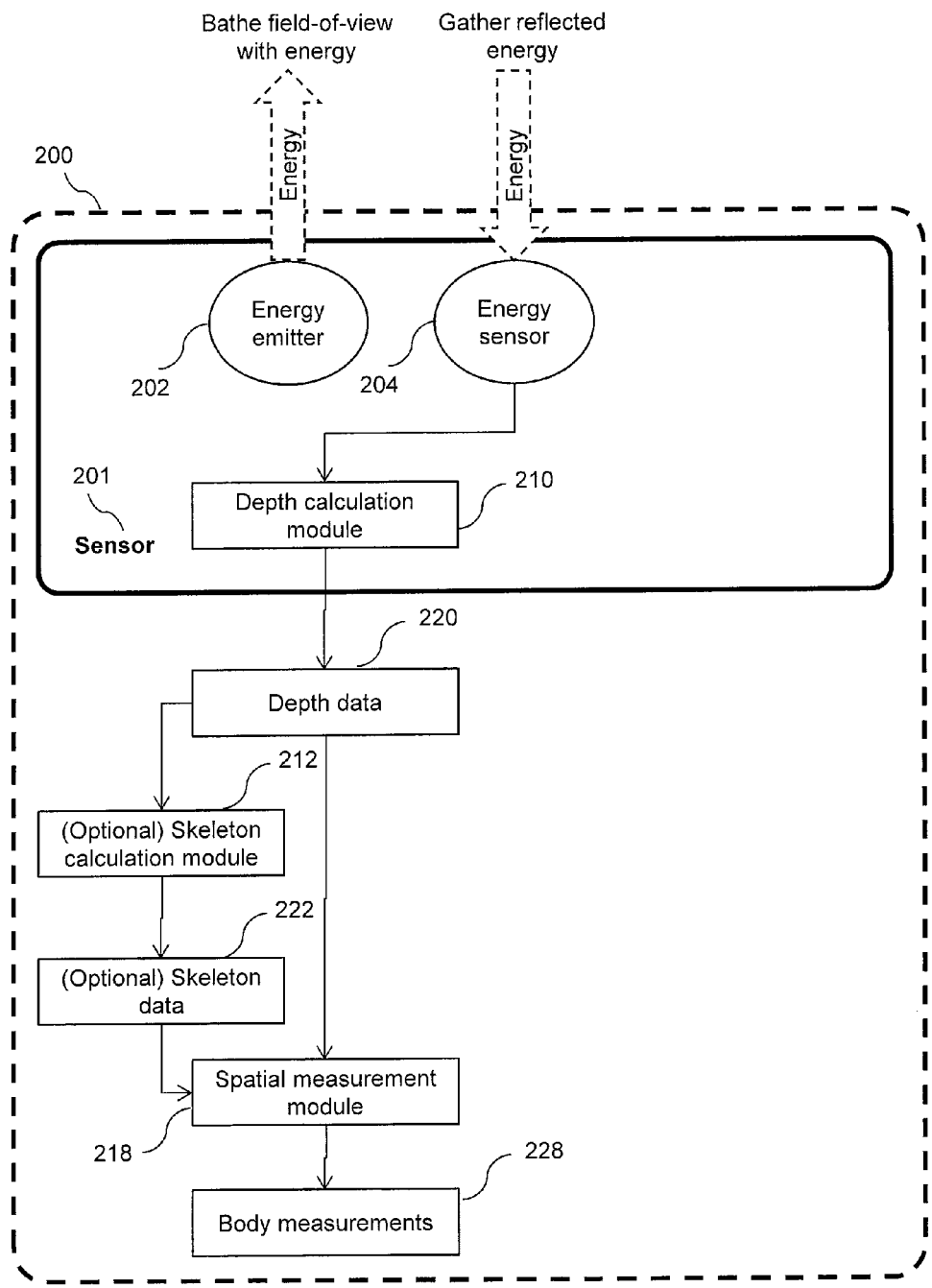

FIG. 2D shows another embodiment of the present inventive method. FIG. 2D is similar to FIG. 2A, except that optional pixel label calculation module 216 and optional pixel label data 226 and optional color image sensor 206 and optional color image data 224 of FIG. 2A are omitted, to emphasize that they are not required for some embodiments of the present inventive method. All items in FIG. 2D correspond to their like-numbered items in FIG. 2A.

Figure 2E:
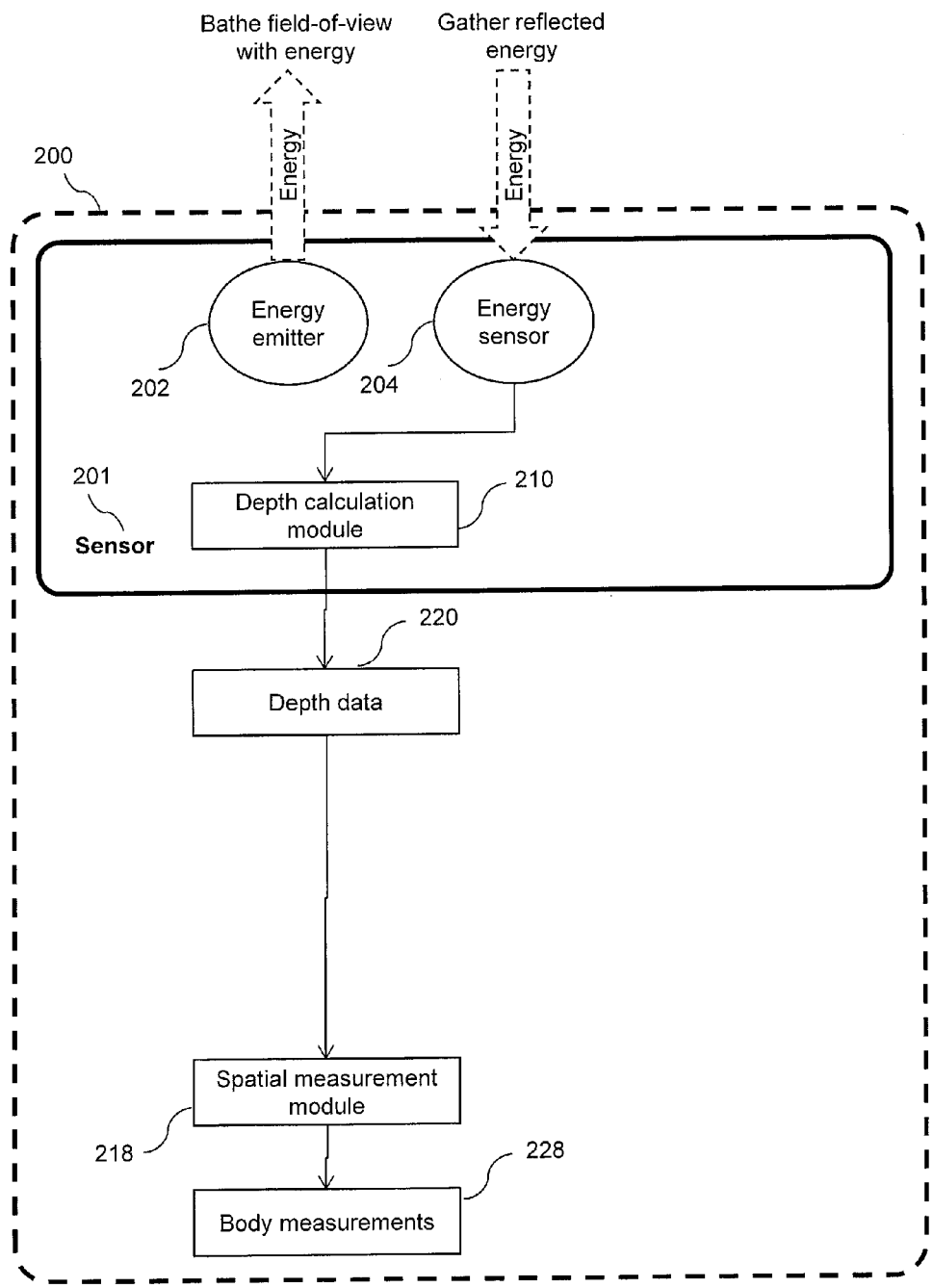

FIG. 2E shows another embodiment of the present inventive method. FIG. 2E is similar to FIG. 2A, except that optional skeleton calculation module 212 and optional skeleton data 222 and optional pixel label calculation module 216 and optional pixel label data 226 and optional color image sensor 206 and optional color image data 224 of FIG. 2A are omitted, to emphasize that they are not required for some embodiments of the present inventive method. All items in FIG. 2E correspond to their like-numbered items in FIG. 2A.

FIG. 2F shows another embodiment 270 of the present inventive method. FIG. 2F shows an example of the present inventive method that uses pattern-deformation and infrared (IR) light to acquire depth measurements. In FIG. 2F, IR pattern emitter 272 is analogous to energy emitter 202 of FIG. 2A. In FIG. 2F, IR pattern sensor 274 is analogous to energy sensor 204 of FIG. 2A. In FIG. 2F, optional color image sensor 276 is analogous to optional color image sensor 206 of FIG. 2A. In FIG. 2F, depth calculation module 280, optional skeleton calculation module 282, depth data 290, optional skeleton data 292, and optional color image data 294, are analogous to their counterparts (respectively) 210, 212, 220, 222, 224 of FIG. 2A.

In FIG. 2F, optional pattern pre-processing module 275 may clean, sharpen, remove noise from, or otherwise modify the information from IR pattern sensor 274. In FIG. 2F, optional color image pre-processing module 277 may clean, sharpen, remove noise from, or otherwise modify the information from optional color image sensor 276. Referring again to FIG. 2A, energy sensor 204 may optionally be accompanied by a pre-processing module (not shown) analogous to optional pattern pre-processing module 275. Referring again to FIG. 2A, optional color image sensor 206 may optionally be accompanied by a pre-processing module (not shown) analogous to optional color image pre-processing module 277. Alternatively, in FIG. 2A, any pre-processing—if needed—analogous to components 275 and 277 of FIG. 2F may be incorporated within (respectively) energy sensor 204 and optional color image sensor 206.

In FIG. 2F, depth calculation module 280 draws on the information transmitted by optional pattern pre-processing module 275—or directly on IR pattern sensor 274, if 275 is not present—and may optionally also draw on the information transmitted by optional color image pre-processing module 277—or optionally directly on optional color image sensor 276, if 277 is not present—in order to calculate depth data 290. The color image itself, if present, may also be maintained separately as optional color image data 294. The depth data calculation module 280 does not require any information from color image pre-processing module 277 or optional color image sensor 276, but may optionally utilize such information to improve the accuracy of depth data 290.

The data from any combination of IR pattern sensor 274, optional pattern pre-processing module 275, optional color image sensor 276, optional color image pre-professing module 277, and depth calculation module 280, may be used by optional skeleton calculation module 282 in order to construct optional skeleton data 292, consisting of (as described previously) a set of approximate spatial locations of anatomic joints (for example, the [x, y, z] locations of shoulder, hip, and ankle). Similar to the depth calculation module 280, the skeleton calculation module 282 requires only information from IR pattern sensor 274 and/or optional pattern pre-processing module 275, and preferably information from depth calculation module 280.

Although not shown in FIG. 2F, components analogous to optional pixel label calculation module 216 and optional pixel label data 226 of FIG. 2A may be placed in an analogous relationship in FIG. 2F as their counterparts in FIG. 2A. For example, an optional pixel label calculation module in FIG. 2F (not shown) could receive the same inputs as optional skeleton calculation module 282, and produce optional pixel label data (not shown), as described previously. For brevity, FIG. 2F does not display such analogs to optional pixel label calculation module 216 and optional pixel label data 226 of FIG. 2A.

Once the input data for body measurements (depth data 290, optional skeleton data 292, optional color image data 294, and/or optional pixel label data [not shown]) are obtained, the system 200 may utilize a computer 298, including a processor 295, RAM 296, and ROM 297, to execute a series of operations on the input data in order to produce measurements of the user's body surface, as described further below. Alternatively, such processing may be performed by dedicated hardware chips and circuits, each of which may have their own internal processor.

The resulting body surface measurements may be placed into a data storage device 284, shown on a display device 285, and/or transmitted over a communication interface 286, such as the Internet. The system may be operated by the user through user input such input may include hand gestures, voice commands keyboard mouse, joystick, game controller, or any other type of user input.

In some embodiments of system 270, the depth calculation module 280 is a component of (or calculated by) computer 298, rather than sensor portion 271. In some embodiments of system 270, the optional skeleton calculation module 282 is a component of (or calculated by) computer 298, rather than sensor portion 271. In some embodiments of system 270, the optional pixel label calculation module (not shown) is a component of (or calculated by) computer 298, rather than sensor portion 271. In general, depth data 290, optional skeleton data 292, and optional pixel label data (not shown) may be generated by modules at various points within system 270, so that their generation is not limited to sensor portion 271.

Because system 200 and system 270 perform similar functions, and share similar inputs and outputs, we will use "system 200" herein to refer interchangeably to both of system 200 and system 270, unless otherwise noted. Similarly, and for the same reasons, sensor portion 201 and sensor portion 271; energy emitter 202 and analogous IR, light emitter 272; energy sensor 204 and analogous IR pattern sensor optional color image sensor 206 and 276; depth calculation module 210 and 280; optional skeleton calculation module 212 and 282; depth data 220 and 290; optional skeleton data 222 and 292; optional color image data 224 and 294; win each be referred to interchangeably, unless otherwise noted.

The system 200 (or 270) may measure the user extremely quickly, and with requirements to pose or position the body. In particular, for an individual measurement of the user, the system 200 requires only a single data-snapshot of the user. Thus, in some embodiments, the user may need to stand relatively still for only a predetermined amount of time, for example 0.001 second to 0.1 second, which in an optical camera, may be determined by the amount of lighting, shutter speed, and aperture size. Other types of image capture or energy capture devices may operate on a much faster basis so that such capture is substantially instantaneous, at least from the perspective of the user.

In other embodiments, the user need not necessarily stand in one position or maintain a particular position for any amount of time, and may be able to move real-time within the field of view of the capture device. Individual measurements from different data-snapshots may also be combined or operated upon further, for example by adding them or averaging them, as described below.

The term "data-snapshot" or "snapshot", as used herein, refers to a single set of depth, and/or image, and/or skeleton data, and/or pixel label data, wherein the data are gathered substantially simultaneously with each other. As noted previously, a single data-snapshot cannot account for any "invisible" or "darkside" aspects of objects in the field-of-view. Where necessary to complete a measurement, therefore, the system 200 "fills in" for invisible aspects by using heuristics that may take advantage of the symmetry of the human body—for example, by doubling a visible half-circumference to estimate the full circumference of a limb. This process is described in further detail below.

The original construction of optional skeleton data 222 may utilize multiple calculations on depth and/or image data over time. The system 200 is agnostic as to the means by which optional skeleton data 222 are generated. From the point of view of the system 200, a single—substantially instantaneous—data-snapshot of depth, and/or image, and/or skeleton data, and/or pixel label data, is sufficient to obtain a particular body surface measurement, regardless of the prior post-processing that was necessary to generate the content of that data-snapshot.

Similarly, the original construction of depth data may utilize multiple calculations on data received from either energy sensor 204 or optional color image sensor 206 individually, or from both energy and color image sensors 204 and 206 collectively over time. For example, a particular image received at one moment in time by either energy sensor 204 or optional color image sensor 706 may serve as a so-called reference image at a subsequent moment in time, such that two or mote images taken slightly apart in time are used to calculate depth data. Again, the system 200 is agnostic as to the means by which depth data, including depth data 220, are generated, including image processing that may occur over time, or different physical methods such as time-of-flight, LIDAR, or pattern deformation.

Through the use of a substantially instantaneous snapshot of data, gathered from one or more stationary cameras, the system 200 avoids the use of a 3D scanner, as well as of wearable markings. As is described further below, this method also avoids, the need for manual intervention—in particular, the need for a second person to conduct body measurements. Some embodiments of the system 200 may be thought of as draping "virtual measuring tapes" in three-dimensional space on top of different parts of the user's body, simultaneously and almost instantly, acting as a sort of "virtual intelligent tailor."

In some embodiments of system 200, energy sensor 204 and optional color image sensor 206 may be placed near each other, as a substantially co-located array, rather than being physically dispersed throughout different points on the perimeter of a field-of-view. Such co-location is ideally as close as possible in order to have the field-of-view be similar for each sensor. The feasible co-location separation distance depends upon the size attic physical components. For example, if energy sensor 204 and optional color image sensor 206 are instantiated as CMOS chips, the chips and their supporting electronics and optics may be placed such that their borders are, for example, approximately 5 mm apart, and the centers of their lenses are, for example, approximately 2 cm apart.

In general, the co-located sensors are preferably positioned with a separation distance of millimeters to centimeter, although smaller and larger distances are possible. Similarly, the angles of view of the co-located, sensors are preferably within a few degrees of each other. This means that embodiments of the present system and method may be very compact and portable, e.g., fitting easily on a shelf or at the base of a television at home.

Depth calculation module 210, optional skeleton calculation module 212, optional pixel label calculation module 216, spatial measurement module 218, and all other modules described herein, may be implemented in circuitry as a physical component or processing element, whether integrated or discrete, or may be implemented to the extent possible, in software to be executed by the processor or specialized processing circuitry.

The depth data 220 might be relative, instead of absolute—that is, a depth pixel value of "8" may delineate a distance that is twice as far as a depth pixel value of "4", without specifying how many absolute centimeters in the real world correspond to values of "8" or "4". However, the system 200 necessarily requires a means to measure real-world distances. For this reason, the system 200 may employ a calibrator. The purpose of the calibrator is to scale depth bitmap pixel distances to real-world physical distances. The preferred shape of the calibrator is spherical, so that its widest dimension is constant regardless of the angle from which it is viewed.

The calibrator is preferably given either a unique thermal (i.e., infrared) or color signature (e.g., neon green), so that it may be easily distinguished from other objects within, respectively, either a depth or color image bitmap. Because the calibrator is of known physical dimensions, its extent along die x and y axes (image bitmap) and z axis depth bitmap) allows physical distances to be mapped to pixel distances along all three axes. These mappings are accomplished using scaling factors referred to herein as "calibration metrics". In some embodiments, the calibrator may be used, while in other embodiments it may be omitted.

FIG. 3 shows the use of a spherical calibrator 300. The system 200 first identifies which pixels in the field-of-view (FOV) correspond to the calibrator preferably using the calibrator's unique signature to distinguish it from other objects in the data bitmaps. The system 200 then determines the number of pixels that correspond to each of the x, y, and z extents of the calibrator in physical space. FIG. 3 shows an example where a depth bitmap returns a distance of 10 pixels or the closest point of the calibrator in z-space, and a distance of 30 pixels for the furthest point of the calibrator in z-space.

Assuming that the calibrator 300 is known to be, say, 8 cm in diameter, it follows that 20 (equal to 30-10) pixels along the z-axis occupies 4 cm (equal to half of the diameter) of physical space. This ratio of 20 pixels to 4 cm is the z-axis; calibration metric. Similar metrics may be derived for the x-axis and y-axis. Subsequent body surface measurements may then be calibrated using these metrics: for example, it the user's neck circumference were found to be 200 pixels along the x-axis, then a calibrator metric of 20 pixels to 4 cm would indicate that the neck circumference was 40 cm in the physical world.

Note that in FIG. 3, the X axis is labeled as "−X". This is because the positive direction of the x-axis is to the left of the sensor, and the negative direction of the x-axis extends to the right of the sensor.

As disclosed, in a preferred embodiment, the calibrator 300 may be spherical. In some embodiments, the calibrator 300 is substantially like a spherical ball used in a sports game, e.g., tennis ball, golf ball, Ping-Pong ball, or basketball. However, many other embodiments of the calibrator 300 are possible. For example, the calibrator may be a shallow fence that is placed upon the floor surrounding the user; or the calibrator may be one or mote L-shaped towers, that are arrayed around the user. Some attributes for any calibrator are 1) it is easy to distinguish from other objects in the FOV, and 2) it provides calibration metrics alone at least one, and preferably alone all three, axes: x y, and z.

Note that if the depth calculation module 210 is inherently able to deliver reliable absolute measurements in physical space, then the calibrator may not be needed. For this reason, the calibrator is optional. One embodiment of the system 200 makes use of the calibrator 300, due to the difficulty of establishing precise real-world depth data from non-calibrated 2D bitmaps—to the difficulty experienced by an human being eyeing a scene and then trying to judge the absolute size of objects in those scene, down to the centimeter level, merely by evaluating their relative sizes to each other. In other words, the depth data 220 are likely to be reasonably accurate on a relative scale, but not on an absolute scale, and so the calibrator 300 is intended to compensate accordingly.

For a single measurement, certain embodiments of the system 200 requires only a single data-snapshot of the user, taken from a single point of view. This is because the system 200 may use heuristics—such as the inherent symmetry of the human body—to "fill in", or compensate for, any invisible depth or image information that is invisible to the sensor portion 201. Furthermore, multiple measurements may be drawn from a single snapshot.

However, for a measurement of a body portion to be taken, that body portion should be substantially in view of the file sensor portion 201. As a general rule, about half of the body portion is preferably visible to the sensor in order for that body portion to be measured (because symmetry or heuristics can be used to deduce the shape of the other half).

For example, to measure the volume of the abdomen, the user typically substantially faces the sensor; if the user presents a back profile (equivalent to a back view) to the sensor portion 201, then the front of the user is invisible altogether, and the abdominal volume cannot be measured. Conversely, to measure the volume of the seat, aside or back profile of the user may be required, because the seat is invisible from a front view. Similarly, to measure the length or width of a foot, either the foot must be profiled so that the sole of the foot is facing the sensor, allowing both measurements to be conducted from the same data-snapshot; or else the length must be measured on its own front a side profile (of the foot), and the width measured separately using a front back profile (of the foot).

Another reason that multiple data snapshots may be required is due to noise in the system. It the inputs or outputs at any component of sensor portion 201 are noisy—that is, varying randomly or non-randomly, due either to inherent aspects of sensor portion 201 or to external environmental conditions, then multiple data snapshots may be required to extract improved signal from the noisy background. For example, data snapshots may be averaged over time, using signal processing methods, in order to have noise "cancel out" and thereby diminish over time, while constructively adding together (strengthening) the valuable signal. If such averaging over time is performed, then multiple data snapshots may be required for higher-accuracy measurements.

Therefore, although any one measurement may require only a single snapshot, nonetheless, in some embodiments, more than one snapshot may be required to obtain a complete set of desired measurements (e.g., to size someone for a pair of trousers). It is preferable to minimize the number of data snapshots, because the fewer the number of snapshots, the quicker and easier is the sizing for the user. To achieve this goal of minimizing the number of snapshots, some embodiments of the system 200 may minimize the number of separate profiles, or views, that are be presented by the user to the sensor portion 201 for processing.

There are 5 primary profiles, or views, that the user may present to the sensor portion 201:
1) Front profile: the user directly faces the sensor, standing with arms extended horizontally to the side, and hands rotated so that the palms also directly face the sensor.
2) Side profile: the user stands at a ninety-degree angle to the sensor, presenting either the left or right side (due to symmetry, the two sides are equivalent). The user extends both arms directly to the front, so that the arms do not obscure the torso.
3) Back profile: the user stands facing directly away from the sensor, with arms extended horizontally to either side, and hands rotated so that the palms also face directly away from the sensor.

4) Sole profile: the user sits on the floor, facing the sensor, so that the soles of both feet are clearly in view of the sensor.

5) Palm profile: the user stands, facing the sensor, and holds out both arms in front so that the palms of both hands are clearly in view of the sensor.

Many additional profiles, besides the five listed above, are possible—for example, facing the sensor—with arms related at both sides—and so the list of profiles above is not intended to be exhaustive. Additional profiles are within the scope of the system 200. For example, a different set of poses is preferable for disabled persons (e.g., a set of profiles in which the person would sit instead of stand). For example, for shirt-sleeve sizing, a preferred profile may consist of the user placing hands on hips, with elbows bent, corresponding to a pose commonly assumed by customers during the sizing oil shirt sleeve by professional tailors. For example, for bra sizing, a preferred profile may consist of the user facing sensor portion 201, with hands on hips, and rotated slightly either left or right, in order to allow points on the sides and front of the breasts to be acquired and measured by the system 200.

The relationship of measurements to the 5 primary profiles is shown in FIG. 4. For each measurement shown in FIG. 4, the "preferred profile" is the first-choice profile of the user with which to conduct that measurement, and the "alternate profile" is a backup choice that may be used in place of (or in addition to) the preferred profile.

The number of data-snapshots may be minimized as follows. First, a desired collection of measurements is ascertained. For example, these might be the collection of measurements required to fit a shirt or blouse. Such collections may be defined ahead of time, e.g., by predetermined lookup tables, or decided dynamically based on the requirements of the user. Second, the system 200 may access a table similar to that shown in FIG. 4 to determine the minimum set of profiles to fulfill the entire collection of measurements. For example, if the desired measurements are "shoulder-to-wrist length", "shoulder-to-shoulder distance", and "upper-leg circumference", then the minimum number of profiles is equal to one, because all three measurements can be collected from a single snapshot of a front profile of the user.

One way of finding the minimum set of profiles, given a collection of measurements, is to isolate the rows of FIG. 4 that correspond to the desired collection of measurements, and then to add up the number of times each profile occurs across both the Preferred and Alternate columns. A comparison of the profile counts, versus the total number of measurements, gives the minimum number of profiles needed to collect all the measurements. For example, if there are three measurements, and any profile appears three times across all the columns, than that profile alone is the only profile that is needed; otherwise, if any profile appears two times, then that profile and one other are the minimum needed; otherwise, three profiles may be required. This reasoning may be extended to any arbitrary number of measurements.

Figure 5:
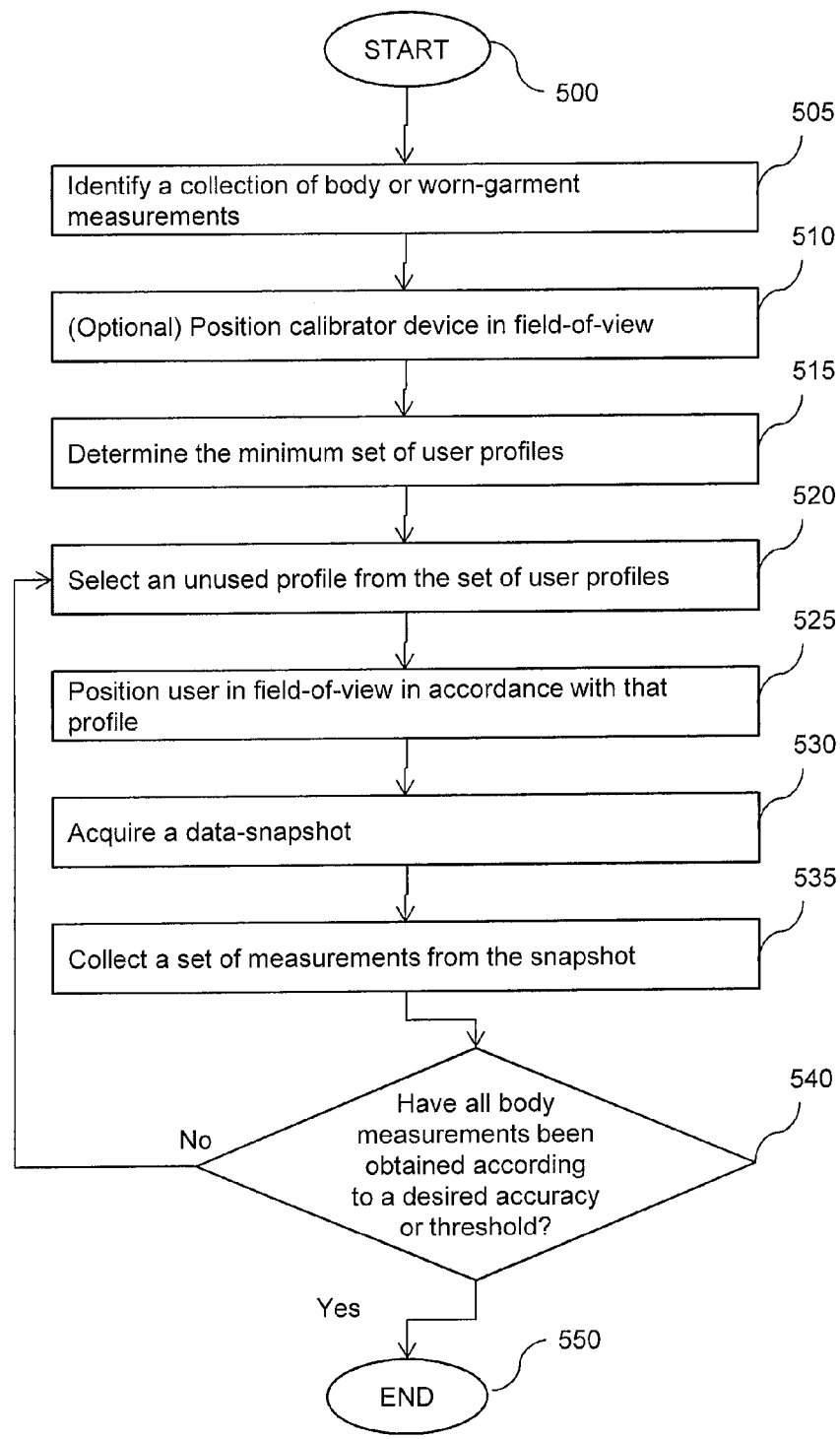
FIG. 5 shows a high-level flowchart according to a specific embodiment.

FIG. 5 shows a high-level flowchart describing a preferred embodiment of the present system and method, beginning at step 500. In Step 505, a collection of body measurements is identified, as described previously. For example, Step 505 might include the collection of measurements required to fit a shirt or blouse. In Step 510, a calibrator device is optionally placed anywhere in the field-of-view (note that the specific sequencing of this step 510 is flexible—in general, the calibrator may be placed in the FOV al any time prior to the first acquisition of a data-snapshot). In Step 515, the minimum set of user profiles that is required to collect the desired measurements 505) is determined, as described previously. In Step 520, an unused profile is selected from the minimum set of user profiles 515.

For example, the user's front profile might be chosen. In Step 525, the user may be prompted to adopt the profile 520. For example, if the front profile was chosen in Step 520, then the user would be prompted to stand facing the sensor, with arms extended to the sides. In Step 530, a data-snapshot is acquired, as previously described. In Step 535, a subset of the collection of body measurements is drawn from the snapshot, as described below. In Step 540, the system 200 checks whether all measurements in the collection of measurements 515 have been obtained. If "no", then Step 520 repeats, selecting an unused profile from the set of user profiles that was generated in Step 515. If "yes", then the current measurement collection process is complete (Step 550).

Because of the user profile minimization process described previously, the user will be prompted to perform the lowest number of poses necessary to collect all the desired measurements; and because a single data-snapshot is virtually instantaneous, this means that embodiments of the present system and method may act very rapidly. For example, a measurement of neck circumference (e.g., for a necklace) may require only a single data-snapshot, occupying literally a fraction of a second—the sizing-and-fitting equivalent of taking a single photo from a digital camera.

As described above, if the system is noisy, then some embodiments of the present inventive method may acquire multiple data snapshots in order to better extract signal from the noisy background. In such cases, Step 540 checks whether all desired measurements have been acquired according to a desired accuracy or threshold. An example of an accuracy might be, continue acquiring and averaging data snapshots until a pre-specified standard deviation of the data value is achieved. An example of a threshold might be, acquiring 60 data snapshots, at a rate of 30 data snapshots per second, and averaging depth map data values across (hem. Another example of a threshold might be, that the user views the results of the data measurement and process and decides whether to continue acquiring additional measurements or not. In general, Step 540 allows any type of calculation or decision-making process to improve signal extraction from noise.

It is also possible for the system to respond, in real-time, to the user's posture and profile, and opportunistically acquire measurements as the user moves around, in any order of measurements. Such embodiments of system 200, which enable real-time interactivity, are described further below and displayed in FIG. 15.

As set forth in FIG. 5 and, more generally in other embodiments, it is possible to perform measurements of not just the user's body surface, but of garments that the user is wearing. Step 505 highlights that worn-garment measurements may be collected instead of, or in addition to, user body surface measurements. For example, the user could put on a favorite pair of jeans, and an accordance with a specific embodiment, measurements may be acquired of the (now being-worn) jeans instead of (or in addition to) the users body surface, for example, by employing the same or similar steps as shown in FIG. 5.

One reason such worn-garment measurements would be valuable is that they could enable new garments to be identified, for example, from a warehouse or an online store that possessed purchasable garments having similar size and shape characteristics to the user's favorite pair of jeans (or any other worn item of clothing). So, in general, the steps in FIG.

5 may apply to either the user's body surface, or to garments that the user is wearing at the time of measurement.

Throughout this document, for purposes of brevity and clarity, we will refer to measurements of the user's body surface; but it should be understood that measurements of garments worn by the user also fall, in all respects, within the scope of the system and method, and that all discussions and figures herein pertain both to the measurement of a user's body as well as to measurement of any garments that may be worn by the user at the time of measurement.

Figure 6:
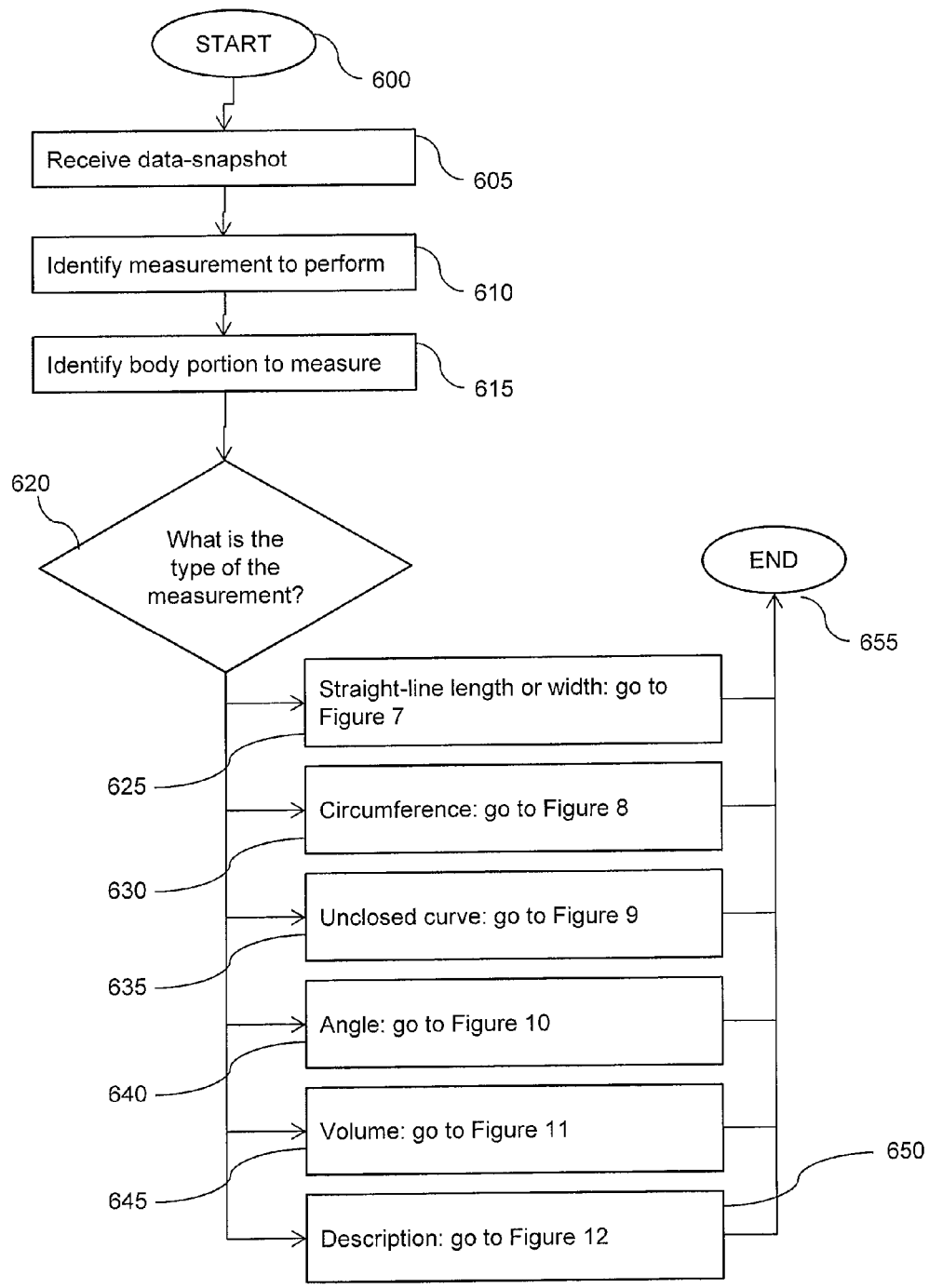
FIG. 6 shows a flowchart to obtain a single measurement according to a specific embodiment.

FIG. 6 is a flowchart showing the steps that are undertaken to carry out an individual measurement, beginning at Step 600. (It follows that Step 535 invokes the steps of FIG. 6 once for each individual measurement that needs to be conducted.) FIG. 6 shows Steps 605, 610, and 615 to, respectively, receive a data-snapshot, identify a particular measurement to perform on that snapshot, and identify which body portion is most relevant to that measurement. For example, Step 605 might receive front-profile data-snapshot; Step 610 might identify that a shoulder-to-shoulder length is the next measurement to be performed, and Step 615 might identity that the torso is the most relevant body portion to measure for that measurement.

Step 610 might be implemented using a queue data structure that is created and initially populated in Step 505. Step 615 might be implemented using a lookup table similar to FIG. 4, but with columns that are body portions (e.g., upper arm, torso, head) rather than user profiles.

There are six primary types of body surface measurements:
1) Straight-line length or width: the linear distance between two points
2) Circumference: the distance of a closed loop (possibly non-circular) around a portion of the body
3) Unclosed curve: the distance along an arbitrary unclosed curve in space that follows the surface of the body
4) Angle: the distance either between two body portions, or between a body portion and a coordinate axis
5) Volume: the volume of a body portion
6) Description: a qualitative description of a body portion, as follows:
    a. Stance (forward-backward): e.g., normal, forward-leaning, backward-leaning, erect
    b. Stance (side-side): e.g., normal, left-leaning, right-leaning, erect
    c. Shoulder slope: e.g., normal, steep, flat
    d. Male chest: e.g., thin, fit, normal, muscular, large
    e. Abdomen (a.k.a. stomach): e.g., thin, normal, medium, large
    f. Seat: e.g., thin, normal, curved, large It should be appreciated that the lists of measurements and of qualitative descriptions shown above are not exhaustive, and that the scope of embodiments of the present system and method is not limited to these specific measurements and qualitative descriptions; additional types of body surface measurements may be identified and carried out by the system.

Embodiments of the present inventive method may use the identification of landmarks on the human body in order to conduct body measurements. A "landmark" as used herein is any point, or border, or in general, any distinguishing location or set of locations, on the body surface, or on worn garments, that may be identified and tracked in three-dimensional space with accuracy sufficient for the body-sizing application at hand. For example, in sizing garments, examples of landmarks might include the spatial position of the head of the ulna of the right arm (for shirt-sleeve-sizing); the lower border of the strap of a worn bra (for bra-sizing); or the upper border of the bridge of the nose (for eyeglass-sizing). For sizing garments, an example of a typical required accuracy might be approximately a half-centimeter to a centimeter; so that, for example, a shirt-sleeve-sizing application might identify and track the 3D spatial location of the head of the ulna for the right arm (among other measurements) within approximately a centimeter accuracy in real-time.

Landmarks are distinguished iron the skeleton data 222 by the precision, reproducibility, and reliability of landmarks. Skeleton data 222, if present, generally consist of approximate locations of nebulously defined portions of the body, or collections of anatomic structures. Skeleton data can be thought of as guideposts general regions of the human body. Most often, they correspond to joints of the human skeleton, such as the shoulder or knee, because machine recognition algorithms may be employed to recognize structures that stay relatively constant in shape while moving, such as arms and legs, and therefore these algorithms may also be used to identify the approximate articulation regions between, say, arms and legs.

An example of skeleton data would be the approximate 3D spatial location of the right shoulder joint. The right shoulder joint is of nebulous definition both structurally and spatially; it consists of multiple anatomic components (portions of the arm, ribcage, surrounding musculature, and so forth) and cannot be precisely located on the human body, only approximately outlined. The skeleton data corresponding to the right shoulder joint, therefore, cannot be used to precisely locate and track (over time) a specific portion of the shoulder, because these skeleton data do not refer to any particular part of the shoulder joint.

Furthermore, skeleton data may be erratic or "jitter" over time, depending on the underlying machine recognition algorithms being employed, again because they don't refer to any specific, particular location in space. Skeleton data are therefore, in general, incapable of being used to conduct precise measurements.

Landmarks are further distinguished from the pixel label data 226 by the precision, reproducibility, and reliability of landmarks. Pixel label data 226, if present, consist of labels that may be applied to individual pixels in depth data 220, or to individual pixels in optional color image data 224. The use of these labels, when they are present, is to distinguish human beings from each other, and from the ambient environment, in a field-of-view.

For example, it depth data 220 were represented by a 640 by 480 pixel depth map of a field-of-view, and if the depth pixel at coordinate (400, 200) corresponded to a distance to a portion of the body surface of a human being; the depth pixel at coordinate (500, 300) corresponded to a distance to a portion of the body surface of a different human being; and the depth pixel at coordinate (20, 50) corresponded to a distance to a door or a wall in the local environment, then depth pixel (400, 200) might be labeled "person #1", depth pixel (500, 300) might be labeled "person #2", and depth pixel (20, 50) might be labeled "non-person".

Similar reasoning applies to optional color image data 724. In sum, if depth data 220 or optional color image data 224 are represented as pixels—for example, in an array or raster representation—such pixels may be attached with labels that distinguish whether the pixel corresponds to a person or a non-person, and if a person, an arbitrary identifies for the person, where such labels are maintained in system 200 as optional pixel label data 226.

As with optional skeleton data 222, the optional pixel label data 226 generally cannot be used to precisely locate and track (over a specific portion of the human body. Optional pixel label data 226 are generally able to signify, for example, that a specific pixel in a particular data snapshot belongs to a surface of a human body and not the ambient environment; or that two different pixels belong to two different human bodies.

Optional pixel label data 266 generally cannot uniquely identify person's identity for example, they cannot label that a person is "John H. Watson who lives at 221B Baker Street", as opposed to "person #1", nor can optional pixel label data generally label a portion of a body (for example, they cannot label that a pixel belongs to "person #1's right shoulder" as opposed to just "person #1"). Optional pixel label data 266 are therefore equivalent to a type of "mask", as the term is known in computer science—applying this pixel label "mask" to depth data 220 or to optional color image data 224 highlights which pixels, if any, correspond to an arbitrarily numbered human being.

Furthermore, similar to optional skeleton data 222, optional pixel label data 226 may be erratic or "jump" over time, depending on the underlying machine recognition algorithms being employed or on the noise the overall system 200. Pixel label data are therefore, in general, incapable of being used to conduct precise measurements.

A wide variety of methods to calculate skeleton data and/or pixel label data, using depth data and/or color image data as inputs, are known in the art, and may draw upon machine learning, statistical, or other technologies or methods. For example, the Microsoft Kinect For Windows Software Development Kit (SDK), from Microsoft Corp. of Seattle, USA, provides software routines to calculate skeleton data and pixel label data (called "player identification" in the Kinect for Windows SDK) from depth data and/or color image data.

For example, the OpenNI open-source software framework, under the auspices of the OpenNI Organization, similarly provides software routines to calculate skeleton data (called "joint data" in OpenNI) and pixel label data (called "figure identification" in OpenNI) from depth data and/or color image data. The Kinect for Windows SDK and the OpenNI framework employ different computational methods, utilize different APIs, have different operating characteristics, and represent information differently. They are mentioned here as illustrations of potential methods to calculate skeleton data 222 or pixel label data 226. The system 200 is agnostic as to the means by which skeleton data 222 or pixel label data 226 are generated. In distinction, "landmarks" as used herein are, by definition, of sufficient accuracy to conduct body measurements suitable for the particular application at hand, including real-time applications such as gait analysis. The word "terminus", as used herein, is a special case of "landmark": a terminus is a landmark that is a single point on the surface of the body (as distinguished from, for example, a border or a curve or a set of locations).

Note that some embodiments the present inventive method use types of energy, such as infrared light from IP light emitter 272, that cannot penetrate worn garments. Other embodiments may employ energy patterns that are able to penetrate worn garments. However, because suck penetrating, radiation may be harmful to human health, or may pose privacy hazards, some embodiments preferably rely on omitted energy of types, such as infrared, that do not penetrate worn garments. For many applications, such as sizing apparel, it is important to be able to measure either the surface of the human body directly, or of interposed worn garments that closely approximate the surface of the human body. As a result, some embodiments may place constraints on the nature of the clothing worn during execution of a particular application. For example, a shirt-sleeve-sizing application may require the user to wear a relatively tight-fitting shirt that does not have collars or cuffs, so that the system 200 can discern the correct underlying shape of the human body. Similarly, for example, a pants-sizing application may require the user to forego baggy cargo pants and the like.

In the descriptions and Figures that follow, it should be appreciated that often only depth data are required to carry out body measurements. For example, depth data alone—or, optionally, a combination of depth data, and the skeleton data that are calculated from the depth data—may be sufficient to carry out a measurement of shirt-sleeve size, because such data may enable identification of all necessary body landmarks (e.g., points on the shoulder, elbow, and wrist) and measure distances between those landmarks, in other cases, depth data are preferably combined with color image data, or a combination of depth data, calculated skeleton data, calculated pixel label data, and color image data may be preferable. In general, identifying the position of a body landmark requires utilizing some combination of depth data 220, optional skeleton data 222, optional pixel label data 226, and optional color image data 224, but the specific combination, and the specific requisite calculations carried out on that combination, differ from landmark to landmark.

For example, a combination of depth data, calculated skeleton data, and color image data may be preferable for determining bra size, because if the user is currently wearing a bra, the image data may be more accurate than the depth data for determining some spatial demarcations or borders of the bra. For example, the lower border of the bra, along the flattened and gradated abdomen, may be difficult to precisely locate using only depth data, but the color difference between the bra material and the exposed skin color beneath it may readily reveal the border with the use of color image data.

Steps 625 through 650 of FIG. 6 refer to additional Figures, respectively, to pursue each specific type of measurement to conduct.

Figure 7:
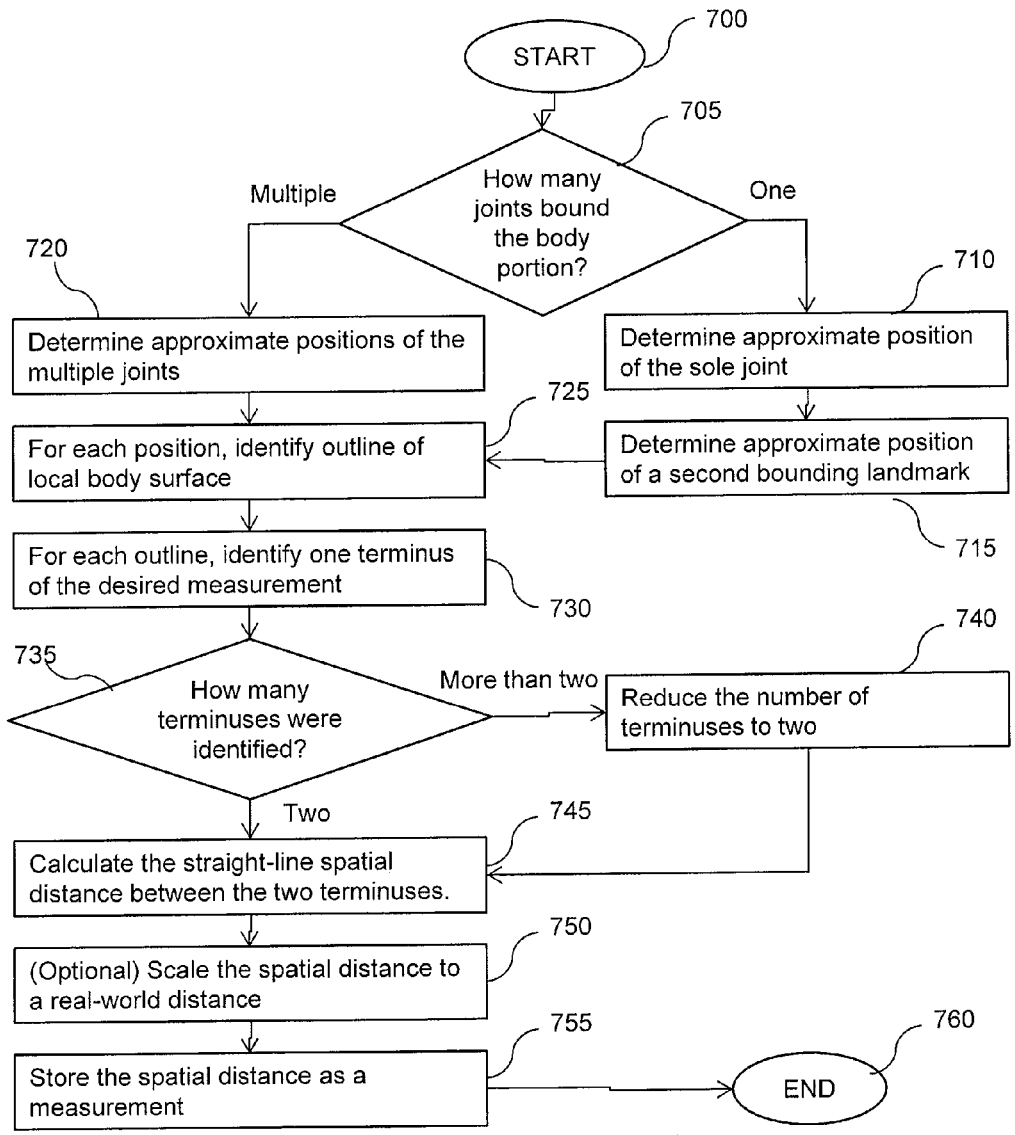
FIG. 7 shows a flowchart to obtain a straight-line length or width measurement according to a specific embodiment.

FIG. 7 is a flowchart showing the execution of a straight-line length or width measurement beginning at Step 700. Step 705 evaluates the body portion that was determined in Step 615 of FIG. 6. For example, this body portion might be the head or an upper-arm. Step 705 counts the number of joints that bound the body portion; this may be easily done using a simple lookup table. If there is only one bounding joint (for example, the only bounding joint for the head is the neck), then Step 710 determines the approximate (x, y, z) position of this sole joint. The preferred way to determine this position is to perform a lookup in the skeleton data 222 supplied by the sensor portion 201. If skeleton data are not available, then image-segmentation methods may be used to identify the approximate location of the bounding joint. In Step 715, a second bounding landmark is determined. For example, an appropriate second bounding landmark for the head is the very top of the head. The position of this bounding landmark is determined, as before, using skeleton data or image-segmentation methods.

Step 705 may alternately determine that multiple joints bound the body portion that was determined in Step 615 of FIG. 6. For example, the upper arm is bounded by shoulder and elbow joints (two joints in total); and the torso is bounded by two shoulder joints and two hip joints (four joints in total). Step 720 determines the approximate position of each joint, again using either skeleton data or image-segmentation methods.

In Step 725, the local body-surface outline, or silhouette, is determined around each joint or landmark position. For example, if a position corresponds to the elbow, then the local silhouette of the elbow is determined. The silhouette may be determined from a combination of depth data and/or color image data and/or pixel label data, using image-segmentation methods. The silhouette may be determined from depth data alone; in some cases, this may result in a degradation of accuracy (for example, if two body portions overlap too closely). The preferred representation of each outline generated by Step 725 is as a "mask" or labeling of pixels that is superimposed on the color image data 224 and depth data 220. Each outline thus describes a set of (x, y, z) locations of pixels that correspond to the body surface local to each joint or landmark position.

In Step 730, each outline from Step 725 is assigned a single terminus. The word "terminus", as used herein, refers to a single point that corresponds to a location on the surface of the user's body; a terminus may be represented, for example, as an pixel location in a depth or image bitmap, or as an (x, y, z) point in space. The assignation of a terminus may be done using heuristic or computational methods. For example, the terminus of an elbow outline might be the point on the elbow midline that is furthest away from the ground in a front profile (in which profile the arm is extended to the side, as described previously).

As another example, the terminus of the top of the head might be the point on the surface of the head that is most distant from the ground. Step 735 invokes Step 740 if more than two terminuses were identified. Step 740 reduces the number terminuses to exactly two, using heuristic or computational methods. For example, if the height of the torso is being measured, then the two shoulder terminuses might be collapsed to a single terminus halfway between them, and similarly for the two hip terminuses, thus reducing the original tour terminuses to just two terminuses.

In Step 745, the straight-line spatial distance between the two terminuses of Step 715 or 740 is calculated. In Step 750, this straight-line spatial distance is optionally scaled to a real-world distance using a calibrator metric, as described previously. In Step 755, the straight-line spatial distance measurement may be stored for further use, and the routine exits at Step 760.

Figure 8:
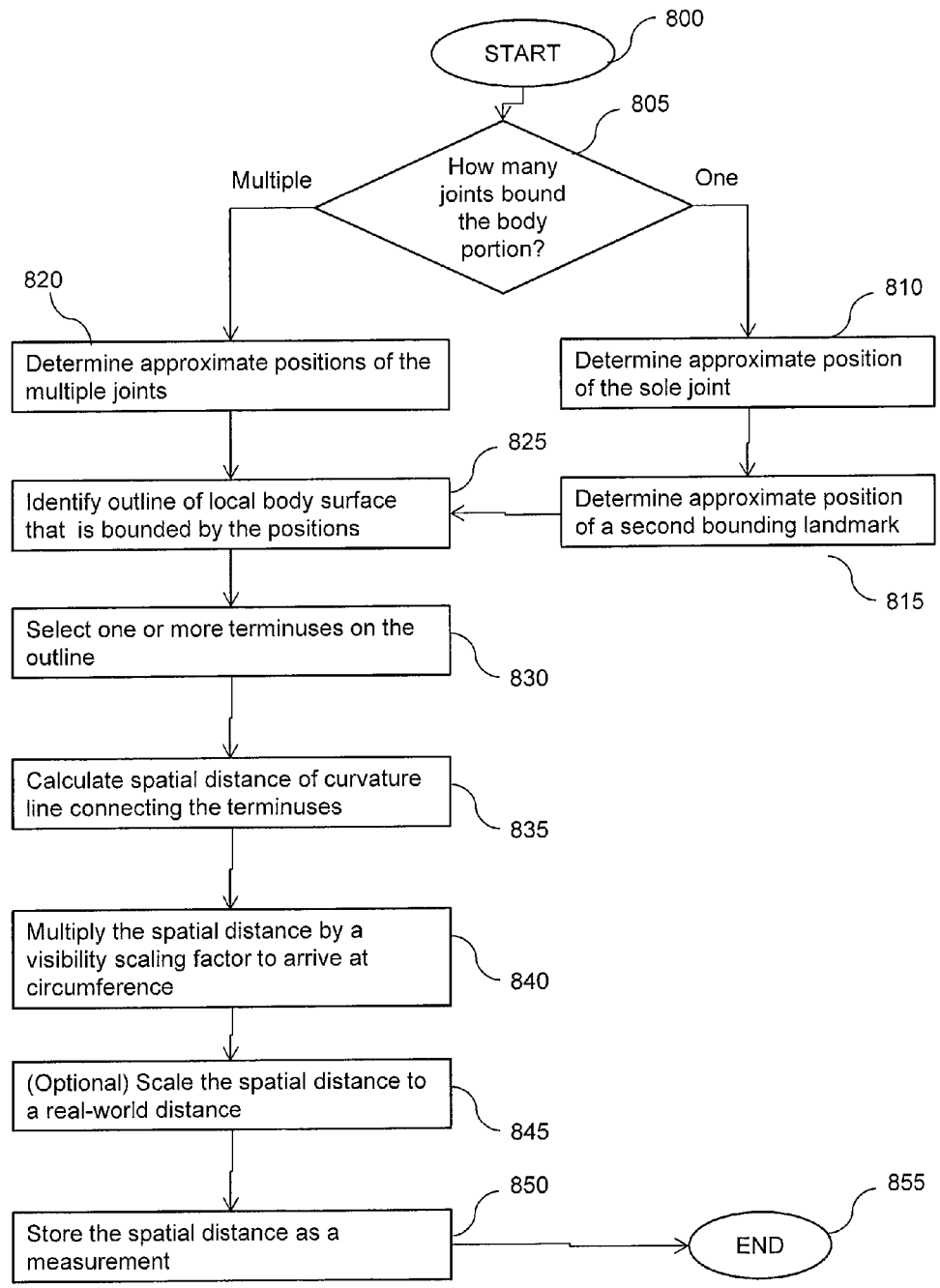
FIG. 8 shows a flowchart to obtain a circumference measurement according to a specific embodiment.

FIG. 8 is a flowchart showing the execution of a circumference measurement, beginning at Step 800. The word "circumference" as used herein refers to the distance along a closed loop in space (which may or may not be circular). Steps 805 through 820 are equivalent to their like-numbered steps 705 through 720, described previously. Step 825 determines the body-surface outline or silhouette, of the body portion bounded collectively by the joint or landmark positions from Steps 820 or 810 through 815. For example, if the shoulder and elbow are the two bounding positions, then Step 825 determines the outline of the body portion that is the upper arm, as bounded by the shoulder and elbow.

This determination of Step 825 is preformed in a similar fashion to Step 725 described previously; however, 825 determines the outline of a single body portion that is bounded by joint or landmark positions, rather than, as 725, the outline of separate areas that are each local to a joint or landmark. This determination 825 provides an incomplete representation of the surface of the body portion in question, because approximately half of the body portion is invisible to the sensor at any one time; for example, only half of the upper arm is visible to the sensor at any one time.

Step 830 may use heuristic or computational methods to assign one or more (x, y, z) terminuses to the outline of the body portion identified in 825. For example, if the upper arm is the body portion of interest, one terminus might be assigned to the point on the outline most distant front the ground (corresponding to the top of the thickest point of the biceps muscle), and the other terminus assigned to the point on the outline directly opposite (corresponding to the bottom of the arm directly below the thickest part of the biceps muscle). Another way to assign terminuses would be to select periodically-spaced points along the path of steepest curvature following the body portion surface.

Step 835 calculates the distance of the curvature, tracking the surface of the user's body, that connects together the terminuses of Step 830. An arbitrary number of terminuses may be so connected, in order to better approximate the real-world distance along the surface of the body portion of interest.

Step 840 multiplies the distance that was calculated in Step 835 by a so-called "visibility scaling factor". This factor compensates for the "invisible" aspect of the body portion. Because a body portion will typically be hall-visible to the sensor, this factor is preferably simply the number 2 (reflecting the approximate symmetry of the human body). The result of Step 840 is a full circumference value.

Step 845 optionally scales the circumference value from Step 840 to a real-world distance using, a calibrator metric, as described previously. In Step 850, the circumference measurement may be stored for further use, and the routine exits at Step 855.

Figure 9:
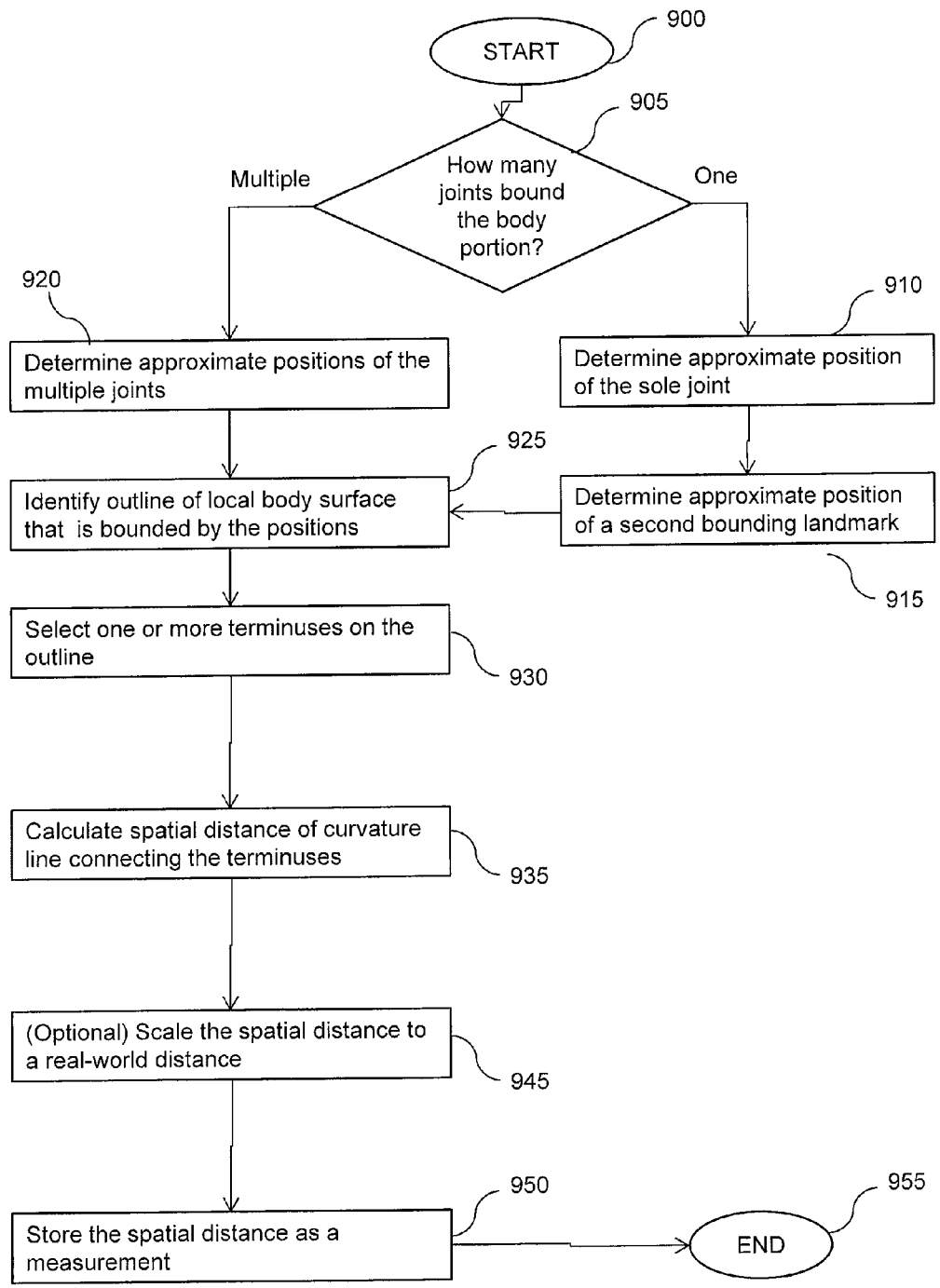
FIG. 9 shows a flowchart to obtain a length of an unclosed curve measurement according to a specific embodiment.

FIG. 9 is a flowchart showing the execution of a distance measurement along an unclosed curve that tracks the body surface, beginning at Step 900. This flowchart is equivalent to FIG. 8, with one exception: the analog of Step 840 of FIG. 8 (multiplying by a visibility scaling factor) is omitted in FIG. 9. This is because, unlike a circumference, it is difficult to estimate the "invisible" aspect of an arbitrary unclosed curve using symmetry or other heuristics.

Figure 10:
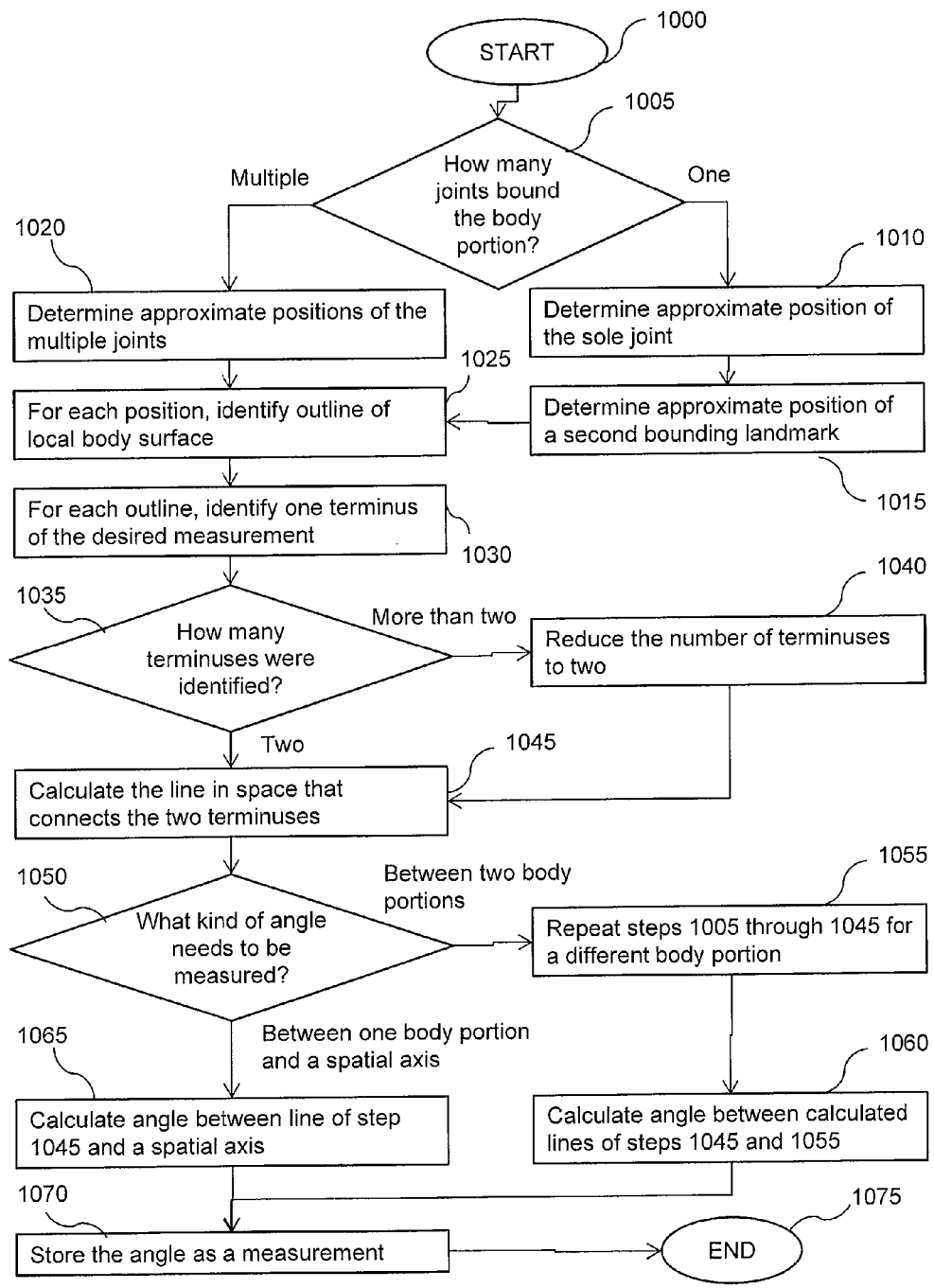
FIG. 10 shows a flowchart to obtain an angle measurement according to a specific embodiment.

FIG. 10 is a flowchart showing the execution of an angle measurement, beginning at Step 1000. Steps 100 through 1040 are the same as their like-numbered steps 705 through 740 in FIG. 7. Step 1045, though, rather than calculate the distance along a line connecting two terminuses as in Step 745, the equation of the fine itself is calculated. Step 1050 then decides between two types of angle calculations.

If an angle compared to a spatial axis (x, y, or z) is desired, then Step 1065 calculates the angle between the line equation of Step 1045 and the appropriate spatial axis. If an angle compared to another body portion is desired (for example, the angle between upper arm and lower arm at point of the elbow), then Step 1055 repeats Steps 1005 through 1045 to arrive at second line equation (corresponding to the second body portion of interest), and Step 1060 calculates the resultant angle between the two computed line equations. Step 1070 may store the angle measurement for future use, and the routine exits at Step 1075

Figure 11:
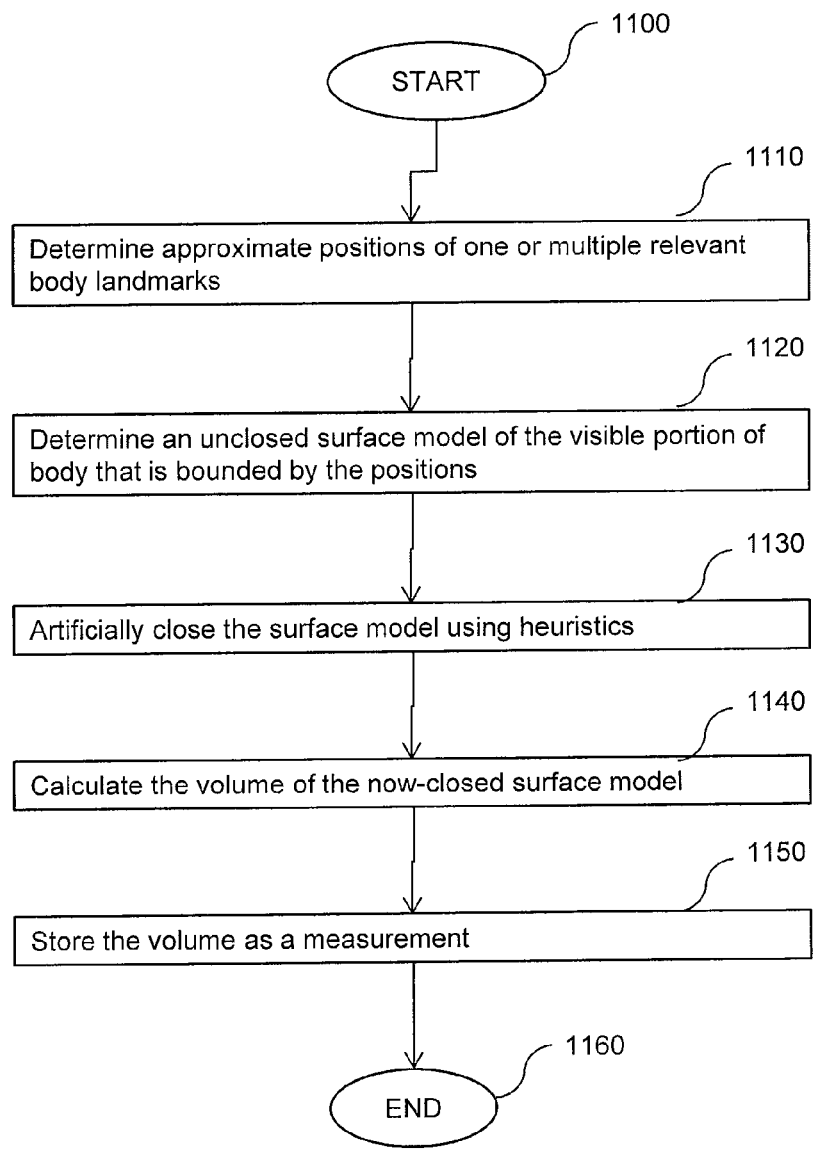
FIG. 11 shows a flowchart to obtain a volume measurement according to specific embodiment.

FIG. 11 is a flowchart showing the execution of a volume measurement, beginning at Step 1100. In Step 1110 the positions of relevant body landmarks may be estimated. For example, landmarks for the abdomen might include the trough between the upper abdomen and the lower thorax, as well as the hips, and the approximate positions in space of those landmarks could be established using, for example, skeleton data or image segmentation methods. Step 1120 uses a data-snapshot to construct an unclosed (that is, incomplete or partial) surface model of the visible portion of the body that is bounded by the positions of Step 1110.

The surface model is necessarily unclosed and incomplete because, as described previously, aspects of the body portion will always be invisible to the sensor portion 201. For example, if the abdomen is viewed from the front, then the back part of the abdomen will be hidden from view of the sensor portion 201. Step 1130 artificially closes, or completes, the surface model using heuristics or approximations, such as symmetry. For example, if the volume of the abdomen is being measured from the front profile, leaving a "hole" in the back of the surface model where the abdomen is invisible to sensor portion 201, then Step 1130 might close the 3D model under the modeling assumption that the back wall of the abdomen is a flat vertical plate.

Step 1140 calculates the volume of the now-closed surface model, and Step 1150 may store the volume measurement for future use. Once the volume measurement has been calculated, the surface model is no longer needed and may be discarded; the system, in some embodiments, may not store any surface model (or portion thereof), in order to preserve the privacy of the user. The routine exits at Step 1160.

Of note, measurement of a surface area of a portion of the user's body—as opposed to a volume measurement—may alternately be performed in Step 1139 by closing the surface model "with itself". In other words, if the surface model is envisioned as a very thin sheet or ribbon hugging the surface or the user's body, then the volume of the surface model is equivalent to an area of the surface of the body. In this way. FIG. 1 can be used to measure an area of the surface of the body as well as a volume of the body.

Figure 12:
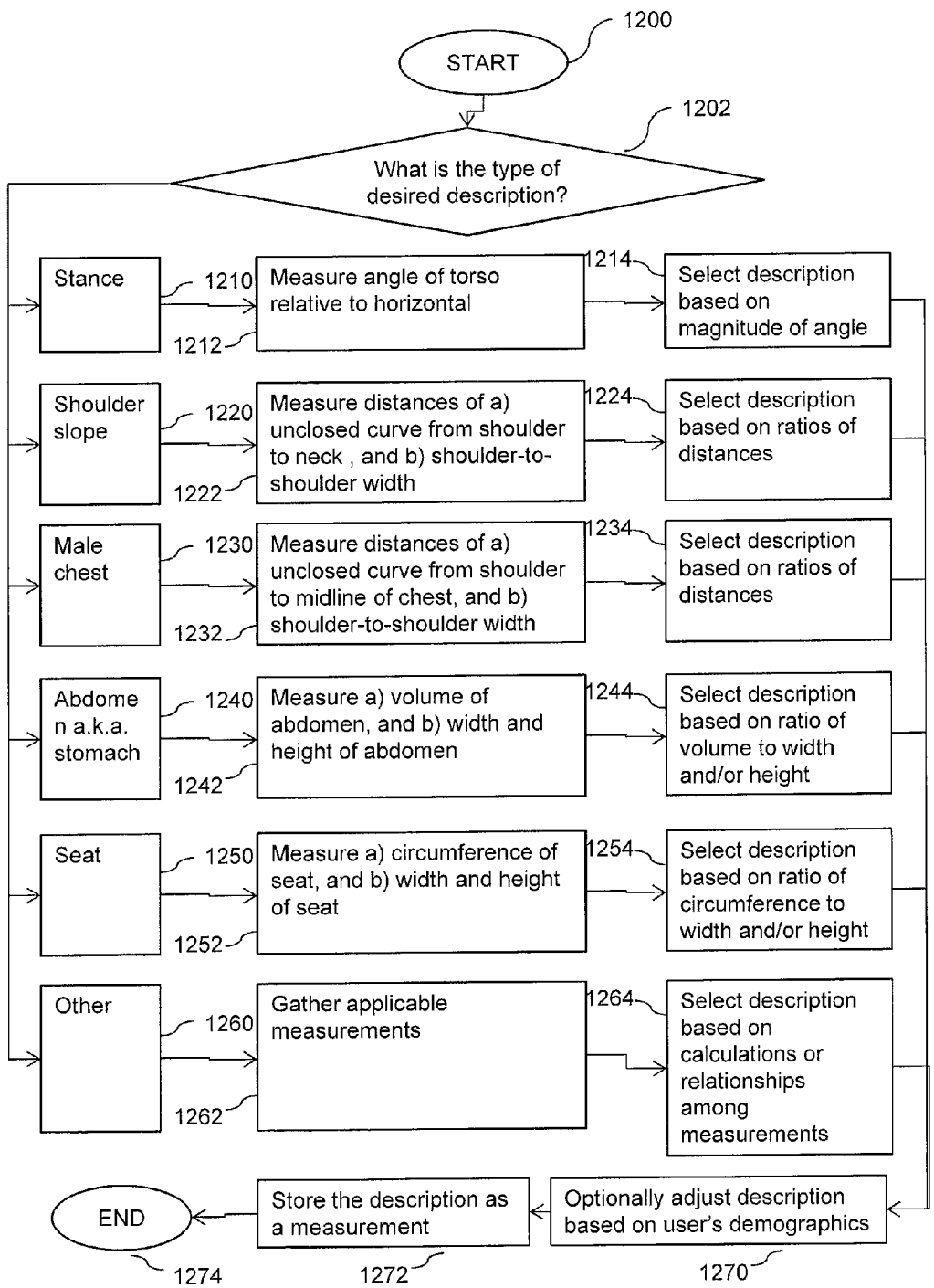
FIG. 12 shows a flowchart to obtain a qualitative description measurement according to a specific embodiment.

FIG. 12 is a flowchart showing the execution of a qualitative description measurement, beginning at step 1200. Step 1202 selects among the various types of descriptions. For a description of stance (e.g., normal, leaning, erect), Steps 1210 through 1214 measure the angle of the torso relative to horizontal, and select a description based on magnitude of the angle. (Note that stance may be either forward-backward or side-side, depending on the data-snapshot profile; this detail is omitted from FIG. 12 for brevity.) For a description of shoulder slope (e.g., normal, steep, flat). Steps 1220-1224 measure several distances related to the shoulder, and select a description based on the ratios of the distances.

For a description of male chest (e.g., thin, fit, normal, muscular, large), Steps 1230-1234 measure several distances related to the chest, and select a description based on the ratios of the distances. For a description at the abdomen a.k.a. stomach e.g., thin, normal, medium large), Steps 1240-1244 measure the volume, width, and height of the abdomen, then select the description based on ratios of those measurements. For a description of the seat (e.g., normal, curved, large), Steps 1250-1254 measure several distances related to the seat, and select a description based on the ratios of the distances.

In general, for any description, as shown in Steps 1260-1254, a set of applicable measurements is first gathered, and then a description is selected based on various calculations or relationships among those measurements (e.g., using ratios). Step 1270 optionally adjusts the description based on user demographics (e.g., age or gender, and Step 1272 may store the description measurement for future use. The routine, exits at Step 1274.

The measurements described across Steps 625 to 650 are not exhaustive. Additional types of measurements may be undertaken by the system 200. Examples of additional potential types of measurements include; the area of a portion of the body surface (e.g., the area that might be occupied by a tattoo); the point of steepest radial curvature of a line or surface along the body surface; and the minimum cross-sectional width or length of a body portion. Embodiments of the present system and method therefore may contemplate or conduct any kind of desired measurements of a user's body, and are not limited to the measurements described in FIG. 6.

FIG. 13 shows an example of a single measurement to measure the circumference of the user's upper arm. The calibrator is placed in the field-of-view, and the user is prompted to present a front profile to the sensor. The approximate positions of the bounding joints of the upper arm (elbow and shoulder) are identified, and the 3D silhouette of the upper arm between them is outlined, approximately forming a half-cylinder. Two terminuses are placed at about the midpoint of the longest dimension of the 3D half-cylinder, and the distance between them (following the shortest path along the surface of the arm) is calculated: this is the half-circumference of the upper arm. The half-circumference is doubled, then scaled using the calibrator metric, to arrive at the final circumference measurement.

Figure 14:
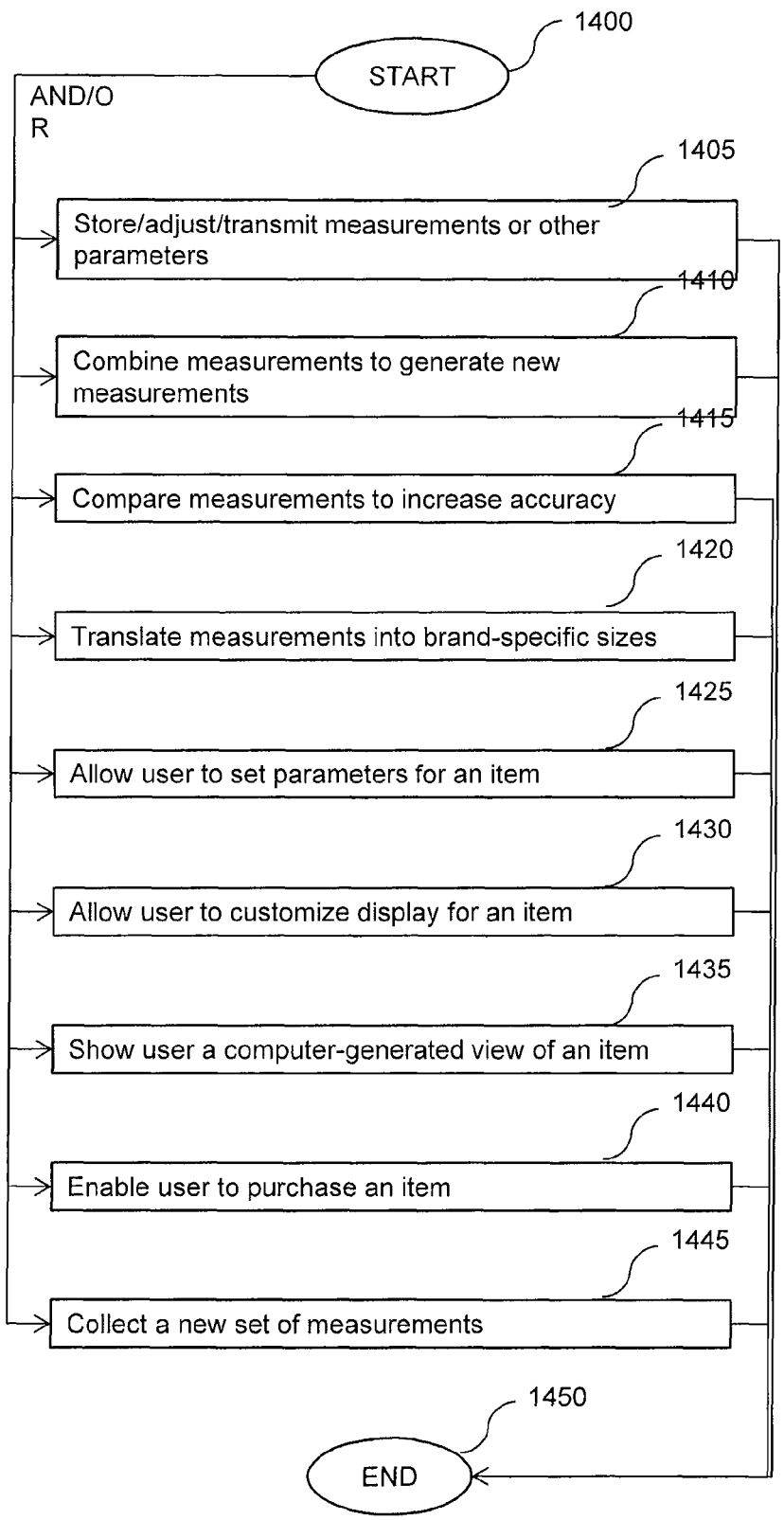
FIG. 14 shows several actions that may be undertaken once a collection of measurements has been completed.

FIG. 14 demonstrates the range of actions that may be performed once a collection of measurements, as described FIG. 5 Step 505, is complete. The routine begins at Step 1400. For example, FIG. 5, Step 550, may invoke the steps of FIG. 14 one or more times. The actions that may be taken once measurements are gathered, as shown in FIG. 14, include:

Step 1405: store, adjust, of transmit the measurements or other parameters. For example, transmission of measurements may occur via the internet, to a facility that can manufacture a garment; of locally, to a disk storage, so as to retain and chart measurements over time. Measurements or other parameters may also be adjusted for example, to match requirements for data structure or for manufacturing intake before being transmitted to a manufacturer. The term "parameter" herein refers to any aspect of an item of apparel, accessory, or prosthetic, including size, shape, fabric type, color, pattern, collar shape, button shape, hem length, graphic, purchase price, purchase date, shipping address, gift note, or any other information concerning an item. (Note that in some embodiments, color image data 224 depth data, 220, and skeleton data 222 are preferably nut retained nor stored by the system 200, in order to preserve the privacy of the user.)

Step 1410: combine the measurements to generate new measurements, e.g., the height of the user may be calculated by summing the heights of head torso, and leg, or the length of two contiguous unclosed curves that were obtained in different data-snapshots may be added together. For example, two approximately orthogonal straight-line measurements may be multiplied (together to calculate the area of a portion of the body surface.

Step 1415: compare different measurements to improve the accuracy of the measuring process. As shown in FIG. 4, some measurements may be obtained across multiple user profiles (for example, upper-arm circumference might be measured in a front profile view, but also in a side profile view). Step 1415 may compare several measurements of the same part of the user's body, in order to improve the accuracy of a "composite" measurement: for example averaging two measurements of the same physical object taken from two different data-snapshots. Step 1415 may also perform an additional calibration cheek on the system as a whole, by taking measurements of known objects using different data-snapshots, and then comparing the measurements to check for consistency.

Step 1420: translate measurements into brand-specific sizes, e.g., the set of body-surface measurements obtained for a trousers sizing may be communicated to the user as being closest in fit to, say, Size 6 Female for the Anne Taylor brand.

Step 1425: allow the user to specify or select parameters for an item (the term "item" as used herein refers generally to an apparel, accessory, or prosthetic item), e.g., color, fabric, collar style, pattern, hem length, preference for form-fit vs. loose-fit, and so on.

Step 1430: allow user to customize the display for an item, e.g., by selecting or designing a logo or other graphic image to be displayed on a manufactured item.

Step 1435: show the user a computer-generated view of an item, e.g., computer-rendered 3D image of the item, possibly superimposed on an image or facsimile of the user.

Step 1440: enable user to purchase an item, preferably online, e.g., by gathering address and credit card number, then transmitting sizing and payment information to a third party for manufacture and shipping of the item.

Step 1445: collect a new set of measurements, by returning to FIG. 5 Step 500. The routine exits at Step 1450.

The actions listed in FIG. 14 may be combined in any number, order, or sequence, and are further not intended to be exhaustive. The scope of the system includes any actions that may be performed upon the gathered measurements.

Figure 15:
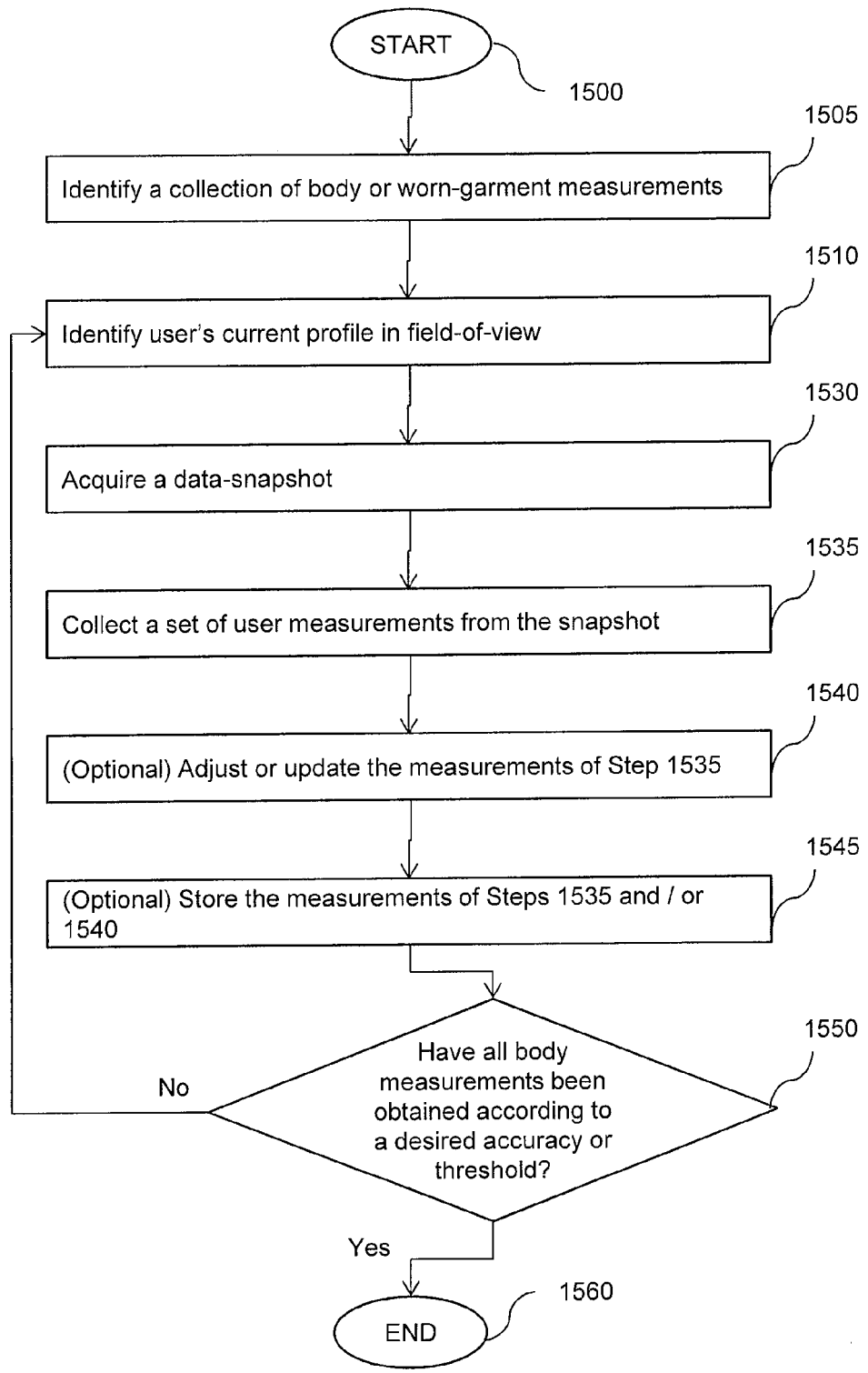
FIG. 15 shows a flowchart to obtain measurements in real-time under conditions of without the requirement for the user to pose.

FIG. 15 shows a high-level flowchart describing a preferred embodiment of the present system and method, beginning at step 1500. The purpose of the process shown in FIG. 15 is to enable garment sizing without the requirement for a user to pose or stay still for a lengthy period of time. In other words, the goal of FIG. 15 is to opportunistically acquire measurements in real-time, while the user moves around naturally. Although not shown in FIG. 15, a calibrator device may optionally be utilized in an analogous fashion to FIG. 5. In Step 1505, a collection of body or worn-garment (i.e., garments that are currently being worn by the user) measurements is identified, as described previously.

Step 1510, the user's current profile is determined. For example, if the user happens to be facing the sensor portion 201 straight-on, then the current profile is a front profile; or, if the user happens to be turned sideways to the sensor portion 201, then current profile is a side profile. There are many different ways to determine the user's current profile.

For example, one way is to evaluate the relative approximate positions of the user's joints, such as shoulders and knees, relative to each other and/or to the sensor portion 201. For example, another way is to apply facial recognition technologies to find the user's face and, if estimate the angle of the face relative to the sensor portion 201.

Optionally, the detected profile may be communicated to the user in Step 1510, or at any other point in FIG. 15. For example, a screen display may indicate to the user that system 200 has identified the user to be in (for example) front profile. The user may then respond or adjust to the detected profile. For example, if the user intends to present a side profile to system 200, but the system 200 erroneously detects a front profile, the user is given an opportunity to become aware of the error, and may adjust his/her position and stance to aid system 200 in detecting the correct profile.

Once the user's profile has been determined, a data-snapshot is acquired in Step 1530, and a set of measurements is collected in Step 1535. Steps 1530 and 1535 are equivalent to the like-numbered steps in FIG. 5.

Next, the measurements in Step 1535 are optionally adjusted or updated. For example, to measure the shoulder-to-shoulder width of the user, the system 200 might perform a series of measurements over time during which the apparent shoulder-to-shoulder width may vary widely, as the user alternately faced the camera, or turned so present a side view to the camera. The process would then retain the largest such measurement under the assumption that the widest shoulder-to-shoulder measurement acquired by the system 200 would best match the real-world shoulder-to-shoulder distance.

Alternatively, the system 200 may calculate a running average of measurements, for example, by averaging the most-recent 100 measurements of the length of the left arm, so as to dampen signal noise. The purpose of Step 1540, essentially, is to compensate for ongoing motions or varied stances of the user, so that measurements may be acquired or refined opportunistically, even while the user moves about naturally.

In Step 1545, the results of Steps 1535 and/or 1540 may be stored for further use. For example, if averaging certain measurements over time is desired, as described above, then Step 1543 may be responsible for maintaining a stored series of measurements so that the running average may be calculated.

Optionally, the obtained measurements may be communicated to the user in Step 1545, or at any other point in FIG. 15. For example, a screen display may indicate to the user that system 200 has measured the user's sleeve length to be for example) 31 inches. Or, for example, a screen display may draw rendered "virtual measuring tapes" superimposed on an image of the user's body, thus indicating graphically some of the underlying calculations leading to the obtained measurements. The user may then respond or adjust to ale obtained measurements.

For example, if the user notices that the system 200 erroneously placed an end of a "virtual measuring tape" on the user's finger, instead of the correct location on the user's wrist, then the user is given an opportunity to become aware of the error, and may adjust his/her position and stance to aid system 200 in detecting the correct points for the "virtual measuring tape" to lock onto. Thus the system 200 and the user may adjust and respond to each other, interactively, real-time. This interactivity applies whether the user is moving or stationary, as in both cases, the system 200 may continue to acquire data snapshots on an ongoing basis (for example, at a rate of 30 snapshots per second).

If graphical representations are employed by system 200, then to safeguard the user's privacy, it may be desirable to avoid displaying, an image of the user's face or head, while preserving the remainder of the user's body and the communication of measurements. For example, if body measurements are communicated to the user graphically by draping "virtual measuring tapes" onto an image of the user's body, then before displaying the graphical representation, the system 200 may identify the portion of the user's body that represents the face or the head, and "blank out" or delete the visual information corresponding to that portion. In this way, the user's privacy may be safeguarded when needed.

As noted previously, in some embodiments, the system 290 may not gather any color image information at all. In other embodiments, the system 200 may gather color image information only temporarily, in order to use the color image information to carry out a set of measurements, and then immediately afterward discard the color image information. In general, for applications where user privacy is important, it is preferable to either gather no color image data at all; or, if color image data is required for some measurements, to gather color image data only as long as needed to determine the measurements, and then discard the color image data as soon as possible, without further storing or transmitting the color image data.

Step 1550 then checks whether all body measurements have been obtained, to a desired level of accuracy or threshold, and if so, Step 1560 exits the process. For example, Step 1550 might transition to exit if the set of measurements in Step 1545 remains constant within (for example) 1/10 of a centimeter during (for example) 90 contiguous measurements. For example, Step 1530 might transition to exit it the user views a set of measurements on a display screen and chooses to stop acquiring new measurements. Although not shown in FIG. 15 for reasons of brevity, it is appreciated that other decision points, besides step 1550, are possible and would tall within the scope of the present system and method. In some embodiments of the present inventive method, Step 1550 does not exit, but instead may execute indefinitely (for example, to supply ongoing garment sizing for a queue of users).

For example, if the system 200, in following the steps of FIG. 15, failed to opportunistically find all necessary body measurements within an elapsed period of time (say, five minutes), which could occur, for example, if the user did not move about sufficiently to present the prerequisite profiles of FIG. 4 to the sensor portion 201, then the system 200 could optionally switch to the processes shown in FIG. 5, in which the user would be actively prompted to assume the prerequisite profiles.

Figure 16A:
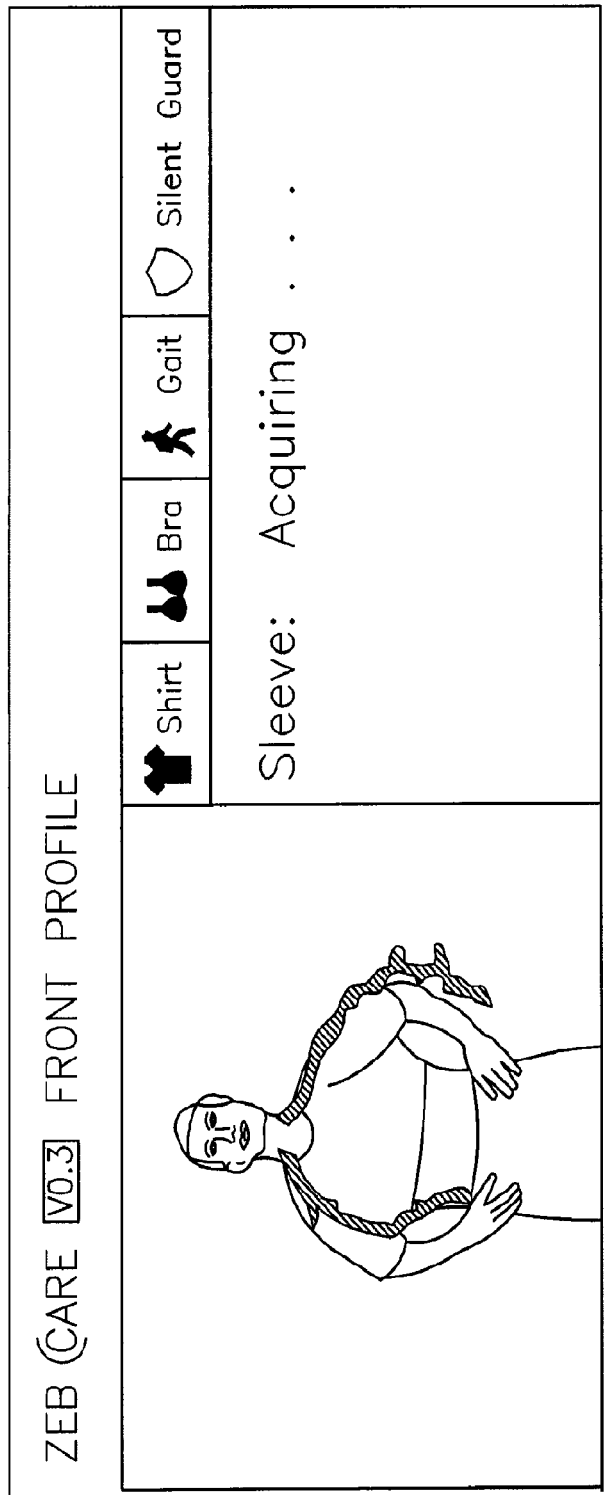
FIGS. 16A and 16B show screenshot examples of a real-world embodiment of the present inventive method.

FIG. 16 shows screenshot examples of a real-world embodiment of the present inventive method. The application in this example is shirt-sleeve-sizing. FIG. 16A corresponds to an early pass through the process steps illustrated in the flowchart of FIG. 15. In FIG. 16A, a user has been identified in the field-of-view of system 200, and the system has begun acquiring a set of predetermined landmarks along the shoulders, arms, and hands, that are relevant to the application of shirt-sleeve-sizing.

The bright white curves or lines FIG. 16A are "virtual measuring tape" indicia, that is, graphical representations of the system's measurement progress, which are updated and displayed to the user in real-time. As the user moves about in real-time, the "virtual measuring tapes" follow the user's motion, also in real-time. The right side of FIG. 16A shows the phrase "Acquiring . . . " to show that the exit condition of Step 1550 in FIG. 15 has not yet been met.

Figure 16B:
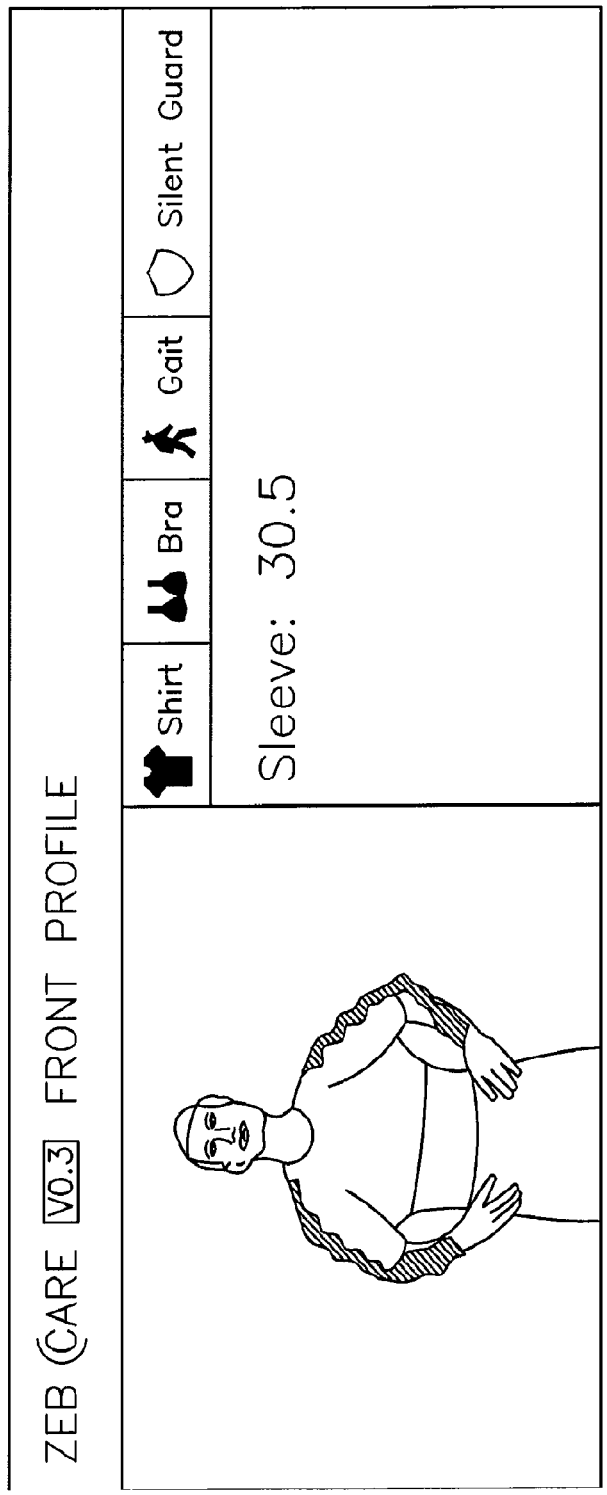

FIG. 16B corresponds to a late pass through the process steps illustrated in the flowchart of FIG. 15. In FIG. 16B, the system 200 has completed a series of body measurements that, over time, met a predetermined threshold of rate-of-change (that is, the change calculated measurement from one fraction of a second to the next fell below a predetermined threshold). The exit condition of Step 1550 in FIG. 15 was met, and thus the right side of FIG. 16B displays the user's calculated sleeve length—in this example, 30.5 inches.

As mentioned earlier, embodiments of the present inventive method may be used in a wide variety of applications. For example, apparel-sizing embodiments of the present inventive method may be employed to carry out the sizing of: shirts, bras, sports coats, pants, shoes, eyeglasses, helmets, body armor, backpacks, swimming suits, and virtually any other type of garment or worn accessory. These are illustrative examples and do not restrict the scope of the present inventive method.

Returning to FIGS. 2A-2F, the system 200 may be embodied as a system cooperating with computer hardware components and/or as computer-implemented methods. The system 200 may include a plurality of software modules or subsystems. The modules or subsystems, such as the sensor portion 201 and the computer subsystem 298, may be implemented in hardware, software, firmware, or any combination of hardware, software, and firmware, and may or may not reside within a single physical or logical space. For example, the modules or subsystems referred to in this document and which may or may not be shown in the drawings, may be remotely located from each other and may be coupled by a communication network.

The system 270 of FIG. 2F is a high-level hardware block diagram of one embodiment of the system 200 used to perform sizing and fitting of an individual for apparel, accessories, or prosthetics. The system 200 may be embodied as a system cooperating with computer hardware components and/or as computer-implemented methods. For example, the subsystems, such as the depth calculation module 210 and all other modules herein, may each include a plurality of software modules or subsystems. The modules or subsystems may be implemented in hardware, software, firmware, or any combination of hardware, software, and firmware, and or may not reside within a single physical or logical space. For example, the modules or subsystems referred to in this document and which may or may not be shown in the drawings, may be remotely located from each other and may be coupled by a communication network.

Additionally, the hardware system 200 shown in FIGS. 2A-2F, including the various cameras and sensors, in one specific embodiment may be provided by one or more commercially-available hardware platforms. For example, sensor portion 201 may be provided by the Kinect System, available from Microsoft Corporation, or by the Xtion/device, available from Asus Corporation. Such commercially available devices may be used to generate depth data and/or color image data and/or skeleton data and/or pixel label data. For example, computer subsystem 298 may be provided by the Xbox System, available from Microsoft Corporation, or by a personal computer, such as one running Microsoft Windows or Apple OS X.

Furthermore, FIG. 2F displays a hardware block diagram of a system computer 298 that may be used to execute software of logic to implement the measurements of the user and other steps disclosed in this document. The computer or computer subsystem 298 may be a personal computer and may include or connect to various hardware components, such as the RAM 296, the ROM 297, the data storage 284, and the like. The computer 298 may include any suitable processor or processing device 295, such as a subsystem computer, microprocessor, RISC processor (reduced instruction set computer), CISC processor (complex instruction set computer), mainframe computer, work station, single-chip computer, distributed processor, server, controller, micro-controller, discrete logic computer, and the like, as is known in the art.

For example, the processing device 295 may be an Intel Pentium® microprocessor, x86 compatible microprocessor, single core processor, dual-core processor, multi-core processor, or equivalent device, and may be incorporated into a server, a personal computer, server, remote computer, cloud processing platform, or any suitable computing platform.

The RAM 296 and ROM 297 may be incorporated into a memory subsystem, which may further include suitable storage components, such as RAM, EPROM (electrically programmable ROM), flash memory, dynamic memory, static memory, FIFO (first-in, first-out) memory, LIFO (last-in, first-out) memory, circular memory, semiconductor memory, bubble memory, buffer memory, disk memory, optical memory, cache memory, and the like. Any suitable form of memory may be used, whether fixed storage on a magnetic medium, storage in a semiconductor device, or remote storage accessible through a communication link. A user input 287 may be coupled to the computer 298 and may include various input devices, such as switches selectable by the system manager and/or a keyboard, or may be conducted independently of such devices, e.g., by using hand gestures or other body gestures, or by using voice commands. The user interface also interface also may include suitable display devices 285, such as an LCD display, a CRT, various LED indicators, a printer, and/or a speech output device, as is known in the art.

To facilitate communication between the computer 298 and external sources, a communication interface 286 may be operatively coupled to the computer system. The communication interface 286 may be, for example, a local area network, such as an Ethernet network, intranet, Internet, or other suitable network. The communication interface 286 may also be connected to a public switched telephone network (PSTN) or POTS (plain old telephone system), which may facilitate communication via the Internet. Any suitable commercially-available communication device or network may be used.

The logic, circuitry, and processing described above may be encoded or stored in a machine-readable or computer-readable medium such as a compact disc read only memory (CDROM) magnetic or optical disk, flash memory, random access memory (RAM) or read only memory (ROM), erasable programmable read only memory (EPROM) or other machine-readable medium as, for examples, instructions for execution by a processor, controller, or other processing device.

The medium may be implemented as any device that contains, stores, communicates, propagates, or transports executable instructions for use by or in connection with an instruction executable system, apparatus, or device. Alternatively or additionally the logic may be implemented as analog or digital logic using hardware, such as one or more integrated circuits, or one or more processors executing instructions; or in software in an application programming interface (API) or in a Dynamic Link Library (DLL), functions available in a shared memory or defined as local or remote procedure calls; or as a combination of hardware and software.

In other implementations, the logic may be represented in a signal or a propagated-signal medium. For example, the instructions that implement the logic of an given program may take the form of an electronic, magnetic, optical, electromagnetic, infrared, or other type of signal. The systems described above may receive such a signal at a communication interface, such as an optical fiber interface, antenna, or other analog or digital signal interface, recover the instructions from the signal, store them in a machine-readable memory, and/or execute them with a processor.

The systems may include additional or different logic and may be implemented in many different ways. A processor may be implemented as a controller, microprocessor, microcontroller, application specific integrated circuit (ASIC), discrete logic or a combination of other types of circuits or logic. Similarly, memories may be DRAM, SRAM, Flash, or other types of memory. Parameters (e.g., conditions and thresholds) and other data structures may be separately stored and managed, may be incorporated into a single memory or database, or may be logically and physically organized in many different ways. Programs and instructions may be parts of single program, separate programs, or distributed across several memories and processors.

Returning to FIG. 14, Step 1440 enables the user of the system to purchase an item (e.g., of apparel, accessory, or prosthetic). The size, shape, or other fitting of this item may be determined by the most recent set of measurements conducted by the system 200; or by any previous set of measurements, conducted by the system 200 in the past, and then stored for later use; or by any set of measurements provided exogenously (e.g., through user input or from a tailor or retail store); or by any combination of subsets thereof, including any combination of individual measurements drawn across different collections of measurements, including measurements acquired by the system 200 or supplied by the user or by other sources.

Similarly, any other parameters that may be used to specify, customize, or otherwise select an item for purchase, may be stored and combined without limit by the system 200. Such parameters may include item color, item pattern, type of fabric, collar shape, hem length, shape of button, and so on, as described in Step 1425. Additional parameters may allow a user to customize a display for an item, such as a logo or other graphic, as described in Step 1430. Additional parameters may link a set or measurements to a brand-specific size, as described at Step 1420, or combine or compare measurements across time or across data-snapshots, as described in Steps 1410 and 1415. The system 200 may acquire, combine, store, or delete any and all such parameters, in any permutation, for indefinite periods of time.

The system 200 may gather specific sets of such parameters and mark or store them as "favorite" or "preferred" combinations. This may be desirable, for example, if the user wishes to re-order items having certain characteristics, without repeating the process of conducting measurements or selecting parameters for those items.

The system 200 may incorporate an online portal through which the user may select, customize, and purchase items. The portal may be a web browser portal, or a portal that is made available a software download to a videogame system, or a portal that is made available through an application download to a tablet computer or a mobile phone, or any other type of online shopping interface. Examples commercially-available web browsers include Microsoft Internet Explorer, Mozilla Firefox, Apple Safari, and Google Chrome. Examples of commercially-available videogame systems include Microsoft Xbox, Sony PlayStation 3, and Nintendo Wii. Examples of tablet computers include Apple iPad and Samsung Galaxy Tab. Examples of mobile phone operating systems include Microsoft Windows Phone, Apple iPhone iOS, and Google Android. Embodiments of the present system and method may incorporate, link to, network with, transmit information to or from, or otherwise employ or utilize any kind of online shopping portal, whether part of the system 200 or supplied by a third party, without limitation.

In Step 1405 the system 200 may transmit measurements or other parameters, for example, to subsystems of system 200 (such as data storage device 284), or to external systems or recipients (such as a facility for manufacturing garments, or an online ordering system for a clothing retailer). The measurements or other parameters may be adjusted in terms of format, units (e.g. metric vs. imperial), or in any way desired. The measurements or other parameters may transmitted to, from, or via an online portal, or to, from, or via any other system or third party. A recipient of measurements or other parameters may be a clothing manufacturer, which utilizes the measurements or other parameters to, for example, select fabric, cut fabric, assemble an item of clothing, and ship it to the user. A recipient of measurements or other parameters may also be a retail store, which utilizes the measurement or other parameters to, for example, select an item of clothing from inventory and ship it to the user. A recipient of measurements or other parameters may also be a social networking system, such as a website or mobile application, which may be part of the system 200 or may be provided or via any, other system or third party, and which may utilize the measurements or other parameters to share the user's preferences or recommendations with other individuals in the user's social network.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A method of determining a spatial distance of curvature along an unclosed curve that tracks a body surface of an individual for sizing and fitting the individual for apparel, accessories, or prosthetics, the method comprising:
capturing data corresponding to the individual positioned within a field-of view of at least one energy emitter and at least one energy sensor, the at least one energy sensor configured to capture energy reflected from the individual and other objects within the field-of-view, wherein the data corresponds to an incomplete representation of a surface of the body of the individual;
generating depth data for the field-of-view based on the captured data from the at least one energy sensor; and
calculating one or more spatial measurements of a portion of a body surface of the individual based on the generated depth data for the field-of-view for sizing and fitting the individual for apparel, accessories, or prosthetics, comprising:
determining an estimated position of each of one or more body landmarks based at least in part on the generated depth data;
determining an outline of the single body portion that is bounded by the estimated position(s), wherein said determining provides an incomplete representation of the surface of the portion of the body surface in question; selecting two or more terminuses of the outline of the single body portion;
determining a spatial distance of curvature connecting at least two of the two or more terminuses using at least one of heuristic technique or approximation; and
storing the spatial distance of curvature as a measurement of the single body portion.

2. The method according to claim 1, wherein the data captured corresponding to the individual within the field-of-view is captured in real-time while the individual moves about in real-time.

3. The method of claim 1, wherein the data captured corresponding to the individual within the field-of-view is captured while the individual remains substantially motionless for a predetermined amount of time.

4. The method according to claim 3, wherein the individual is positioned so that a face of the individual is presented to the at least one energy sensor, with arms of the individual extended outwardly and away from opposite corresponding sides of the individual.

5. The method according to claim 1, wherein the at least one energy emitter emits at least one of a pattern of infrared light, a pattern of laser light, a pattern of ultraviolet light, a pattern of visible light, a pattern of X-rays, a pattern of microwaves, a pattern of radio waves, a pattern of sound waves, a pattern of ultrasound energy, or a pattern of thermal energy.

6. The method according to claim 1, wherein at least one additional energy sensor is positioned so as to view substantially the same field-of-view as the at least one energy sensor, and wherein the at least one energy sensor and the at least one additional energy sensor acquire a substantially non-overlapping spectra of energy.

7. The method according to claim 6, wherein the step of calculating one or more spatial measurements includes utilizing visual data in addition to the generated depth data.

8. The method according to claim 1, wherein skeleton data are calculated from the generated depth data.

9. The method according to claim 8, wherein the step of calculating one or more spatial measurements includes utilizing skeleton data in addition to the visual data and the generated depth data.

10. The method according to claim 1, wherein the step of calculating one or more spatial measurements includes identifying a location in space of at least one landmark on the body of the individual, and wherein the step of calculating one or more spatial measurements includes calculating a length of a curve or a circumference of a portion of the body of the individual, based on the at least one landmark.

11. The method according to claim 1, wherein the step of calculating one or more spatial measurements includes identifying a location in space of at least one landmark on the body of the individual, and wherein the step of calculating one or more spatial measurements includes determining an angle of a portion of the body of the individual relative to another portion of the body of the individual, or relative to a structure in a surrounding environment, based on the at least one landmark.

12. The method according to claim 1, further including generating additional depth data using a second energy sensor, wherein the second energy sensor overlaps in energy characteristics with the first energy sensor.

13. The method according to claim 1, further including positioning a calibrator device having a predetermined shape and predetermined dimension, in the field-of-view.

14. A system of determining a spatial distance of curvature along an unclosed curve that tracks a body surface of an individual for sizing and fitting an individual for apparel, accessories, or prosthetics, the system comprising:
at least one energy emitter for capturing energy reflected from the individual and other objects within a field of view;
at least one energy sensor energy reflected from the individual and other objects within the field of view, thereby capturing data corresponding to an individual positioned within the field-of-view, wherein the data corresponds to an incomplete representation of a surface of the body of the individual;
a depth calculation module for generating depth data corresponding to the individual and other objects in the field-of-view, based on information from the at least one energy sensor; and
a spatial measurement module for calculating, based on the generated depth data, spatial measurements of a portion of a body surface of the individual in the field-of-view for sizing and fitting the individual for apparel, accessories, or prosthetics, wherein the spatial measurement module comprises a processor and a memory storing instructions thereon, wherein the instructions, when executed by the processor cause the processor to:
determine an estimated position of each of one or more body landmarks based at least in part on the generated depth data;
determine an outline of the single body portion that is bounded by the estimated position(s), wherein said determining provides an incomplete representation of the surface of the portion of the body surface in question; select two or more terminuses of the outline of the single body portion;
determine a spatial distance of curvature connecting at least two of the two or more terminuses using at least one of heuristic technique or approximation; and store the spatial distance of curvature as a measurement of the single body portion.

15. The system according to claim 14, wherein the depth calculation module is configured to calculate the depth data from a combination of at least one energy pattern emitted, and at least one reflection of the pattern acquired by the at least one energy sensor.

16. The system of claim 14, including a skeleton calculation module configured to extract skeleton data from the generated depth data.

17. The system of claim 14, wherein the spatial measurement module is configured to calculate body measurements based on a combination of the generated depth data and the extracted skeleton data.

18. The system of claim 14, including an additional energy sensor configured to acquire visible light.

19. The system of claim 18, wherein the spatial measurement module is configured to calculate body measurements from a combination of the generated depth data and data corresponding to the acquired visible light.

20. The system of claim 14, including a skeleton calculation module configured to extract skeleton data from the generated depth data, and including an additional energy sensor configured to acquire visible light.

* * * * *